(12) United States Patent  
Kavehpour et al.

(10) Patent No.: US 10,149,651 B2  
(45) Date of Patent: Dec. 11, 2018

(54) SYSTEMS AND METHODS FOR OBTAINING RHEOLOGICAL PROPERTIES OF VISCOELASTIC MATERIALS

(71) Applicant: THE REGENTS OF THE UNIVERSITY OF CALIFORNIA, Oakland, CA (US)

(72) Inventors: Hossein Pirouz Kavehpour, Los Angeles, CA (US); Pooria Sharif-Kashani, Los Angeles, CA (US); Jean-Pierre Hubschman, Beverly Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 865 days.

(21) Appl. No.: 14/549,372

(22) Filed: Nov. 20, 2014

(65) Prior Publication Data

US 2015/0148649 A1 May 28, 2015

Related U.S. Application Data

(63) Continuation of application No. PCT/US2013/043169, filed on May 29, 2013.

(Continued)

(51) Int. Cl.
*A61B 5/00* (2006.01)
*A61B 3/10* (2006.01)
(Continued)

(52) U.S. Cl.
CPC .......... *A61B 5/6848* (2013.01); *A61B 3/0025* (2013.01); *A61B 3/10* (2013.01);
(Continued)

(58) Field of Classification Search
CPC ....... A61B 5/6848; A61B 3/10; A61B 3/0025; G01N 11/14
See application file for complete search history.

(56) References Cited

U.S. PATENT DOCUMENTS 4,754,640 A * 7/1988 Fitzgerald ............ G01N 11/162
73/32 A
5,705,271 A * 1/1998 Okamura ............ C23C 16/0209
428/141

(Continued)

FOREIGN PATENT DOCUMENTS

JP 07-116125 A 5/1995
JP 2012-505713 A 3/2012

(Continued)

OTHER PUBLICATIONS

Korean Intellectual Property Office (KIPO), International Search Report and Written Opinion dated Jan. 22, 2014, related PCT International Application No. PCT/US2013/043169, pp. 1-11, with claims searched, pp. 2-17.

*Primary Examiner* — Jeffrey G Hoekstra
*Assistant Examiner* — Jonathan M Foreman
(74) *Attorney, Agent, or Firm* — O'Banion & Ritchey LLP; John P. O'Banion

(57) ABSTRACT

Systems and methods are disclosed for obtaining rheological properties of viscoelastic medium, and in particular, in-vivo evaluation of body fluid such as the vitreous. The system includes a needle-like probe having a distal and a proximal end, a rotational actuator, and a sensor coupled to the rotational actuator. The proximal end of the probe is configured for attachment to the rotational actuator. The distal proximal end of the probe has a roughened outer circumferential surface extending axially along at least a portion of the distal end, wherein the roughed distal end of the probe is configured to be disposed within the viscoelastic medium, (Continued)

and wherein the sensor is configured to obtain measurements corresponding rotation of the probe within the viscoelastic medium.

24 Claims, 15 Drawing Sheets

Related U.S. Application Data

(60) Provisional application No. 61/652,663, filed on May 29, 2012.

(51) Int. Cl.
    *A61B 3/00*     (2006.01)
    *G01N 11/14*     (2006.01)
    *A61F 9/00*     (2006.01)

(52) U.S. Cl.
    CPC ............ *A61B 5/4848* (2013.01); *G01N 11/14* (2013.01); *A61F 9/0017* (2013.01)

(56) References Cited

U.S. PATENT DOCUMENTS

| | | |
|---|---|---|
| 2008/0173075 A1 | 7/2008 | Dale |
| 2012/0022354 A1 | 1/2012 | Beyer et al. |

FOREIGN PATENT DOCUMENTS

| | | | |
|---|---|---|---|
| KR | 10-0783614 B1 | | 12/2007 |
| SU | 424049 | * | 9/1974 |
| WO | WO2006/115392 A1 | * | 2/2006 |

* cited by examiner

SYSTEMS AND METHODS FOR OBTAINING RHEOLOGICAL PROPERTIES OF VISCOELASTIC MATERIALS

CROSS-REFERENCE TO RELATED APPLICATIONS

This application is a 35 U.S.C. § 111(a) continuation of PCT international application number PCT/US2013/043169 filed on May 29, 2013, incorporated herein by reference in its entirety, which claims priority to, and the benefit of, U.S. provisional patent application Ser. No. 61/652,663 filed on May 29, 2012, incorporated herein by reference in its entirety. Priority is claimed to each of the foregoing applications.

The above-referenced PCT international application was published as PCT International Publication No. WO 2014/182317 on Nov. 13, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This technology pertains generally to systems and methods for characterization of viscoelastic materials, and more particularly to in-situ characterization of rheological properties of a viscoelastic material.

2. Background Discussion

Rheology, also known as the study of the flow of matter in the liquid or "soft solid" state, is generally performed via a macroscopic rheometer that cannot be used in-situ and requires samples with significantly large volumes. Furthermore, use of existing macroscoping rheometers for delicate viscoelastic samples, and specifically for biological samples, is difficult, and in some cases impossible.

In order to characterize small samples, microrheology using microspheres (e.g. magnetic beads) has been developed; however the use of such microspheres sacrifices accuracy, and results in uncertainty. Microrheology using microspheres has limited applicability, especially in the characterization of biological samples and in-situ characterization of live tissues.

In therapeutic treatment, intravitreal injection of drugs or implantation of intravitreal drug delivery systems have become a more frequent way to administer treatment in different ocular pathologies such as age related macular degeneration, macular edema, endophthalmiti, etc. Most of these therapeutic treatments directly affect viscoelastic properties of the vitreous gel and molecular structures. However, the delivery of drugs to the eyes presents many challenges, most of which are owed to the complexity of the structure of the vitreous and its unpredictable viscoelastic changes during treatment. Therefore, it is essential to systematically monitor such changes in clinical research or treatment in order to optimize the design of drug delivery devices as well as the schedule for intravitreal injection. The main challenge, however, is the fact that its structure is extremely fragile in nature. In order to measure its bulk rheological properties using conventional rheology, the eye must be dissected, and vitreous needs to be removed. This further alters its properties and makes the measurements extremely difficult.

BRIEF SUMMARY

Accordingly, an object of the technology described herein is a microrheology system and methods for in-situ, real time characterization of various viscoelastic materials, such that the target sample does not need to be contained in any special vessel or container. At least some of these objectives will be met in the description provided below.

An aspect of the technology described herein is a method for in-vivo characterization the vitreous, comprising: inserting a needle like probe into an eye; rotating the probe with an approximately constant torque; sensing the amount of rotational displacement caused by the vitreous and determining viscoelastic properties of the vitreous therefrom. In a preferred embodiment, the acquired viscoelastic properties may be compared to a database of fluidic data relating to the vitreous and associated medical conditions to diagnose the risk or the presence of a degenerative or pathologic modification of the vitreous related to known or unknown diseases; determine a vitreous related pathology selected from the group of pathologies consisting of retinal tear, rhegmatogenous or tractional retinal detachment, retinal edema, choroidal detachment, vitreous hemorrhage, and glaucoma; diagnose and prevent vitreous related complications; or quantify the effects of a particular drug or device on the quality of vitreous humor.

Another aspect is a needle-like probe that is capable of being inserted in the cavity or organ (eye, joint or any other cavity or organ) to directly obtain the viscoelastic properties of the body fluid (such as the vitreous), which correspond to its macromolecular structure. In some embodiments, the probe of the technology described herein is used to diagnose the risk or the presence of a degenerative or pathologic modification of the body fluid related to known or unknown diseases, which occur mostly due to the body fluid's (including the vitreous humor) macromolecular organization and viscoelastic properties.

Further aspects of the technology will be identified in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

I. Microrheology Systems and Methods.

Figure 1:
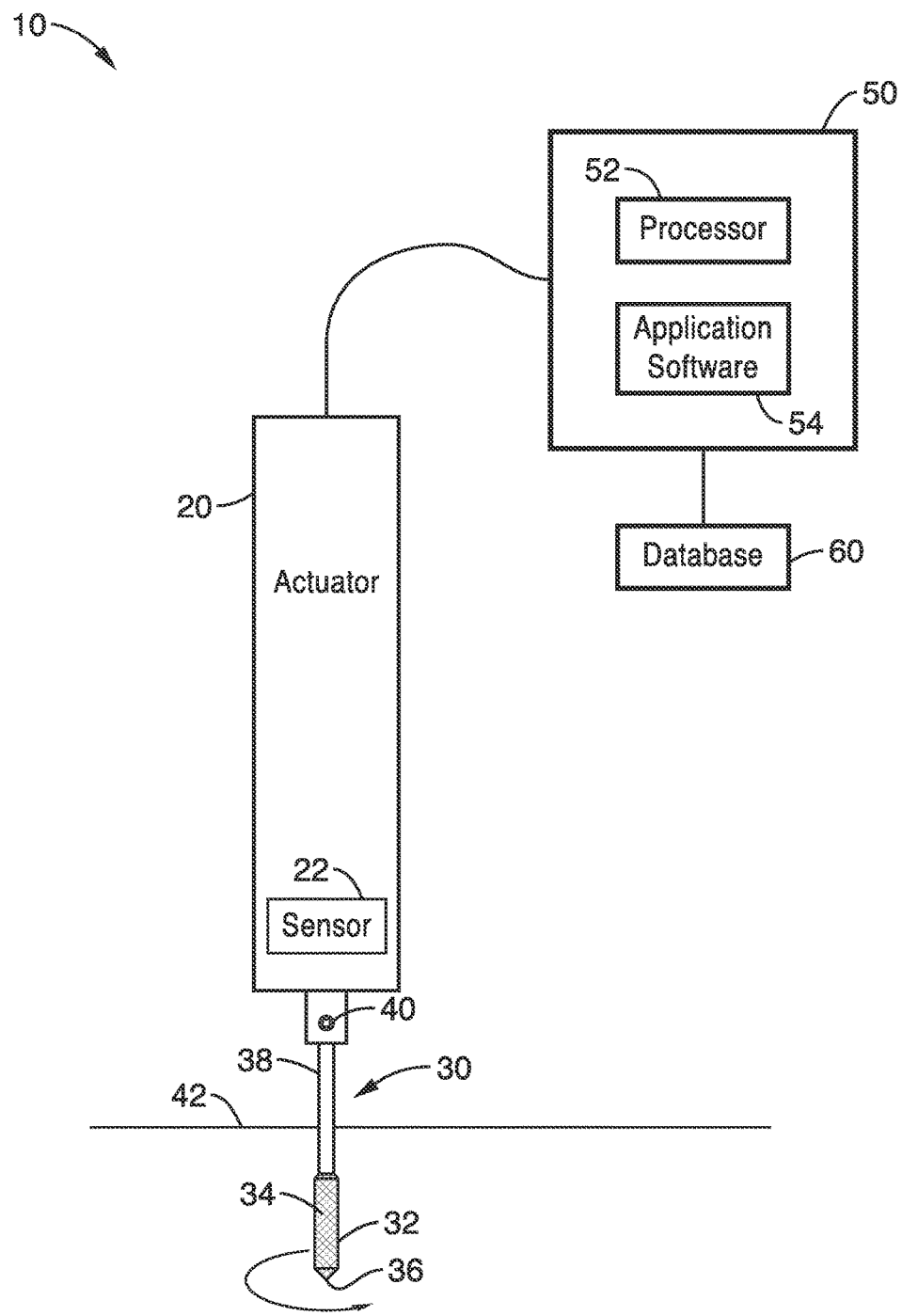
FIG. 1 is a schematic diagram of a system for obtaining rheological properties of viscoelastic medium in accordance with the technology described herein.

FIG. 1 illustrates a schematic diagram of a system 10 for obtaining rheological properties of viscoelastic medium in accordance with the technology described herein. System 10 includes a needle-like probe 30 configured for direct insertion and actuation into the target medium 42. The probe is coupled to an actuator 20 via fastening means 40 (e.g. a set screw or like fastener). Actuator 20 is configured to provide rotational motion to the probe 30, upon which resistance generated from the medium is detected by sensor 22. The readings from the sensor 22 are input to computing device 50 for processing via application software 54 via processor 52. Application software is preferably configured to obtain one or more rheological properties of the target viscoelastic medium 42, and provide further determinations of the medium with use of a reference database 60.

Figure 2:
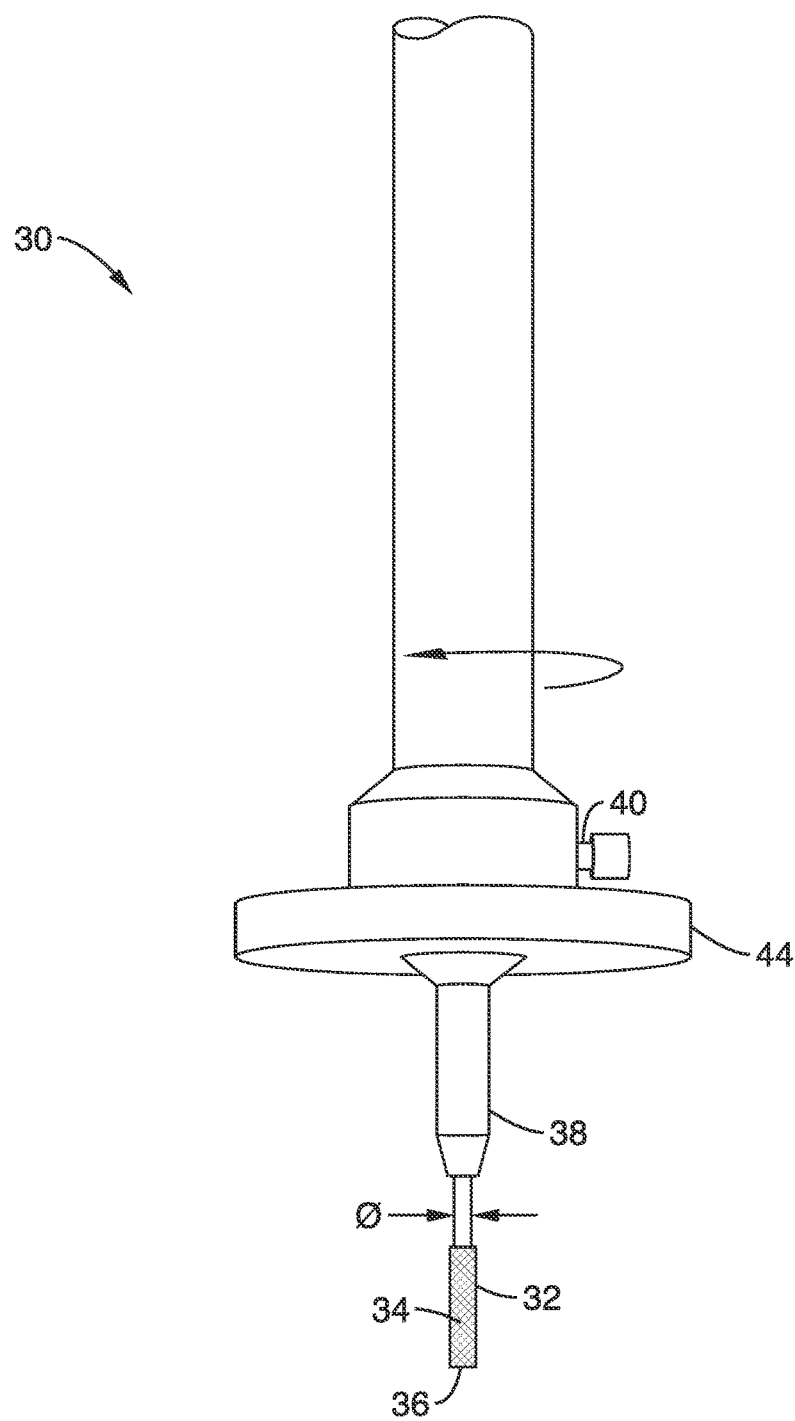
FIG. 2 shows a perspective view of a micro-probe used in accordance with the system of FIG. 1.

As seen in further detail in FIG. 2, the probe 30 comprises a cylindrical elongate body 38 with a distal end 32 having a roughened circumferential external surface 34 extending axially down a length of the distal end 32. In a preferred embodiment, the roughened surface 34 may comprise a diamond-bit coating, or the like, to prevent slippage between the probe 30 and the medium 42. The distal tip 36 may be sharp to promote insertion of the probe 30 into the medium. In the embodiment shown in FIG. 2, the probe 30 may comprise a flange 44 to promote attachment to a specific rheometer/actuator 20.

In a preferred embodiment, the cylindrical probe 30 is sized to a diameter $\phi$ sufficient to obtain real-time rheological properties of viscoelastic materials. The probe 30 can be used for sample volume as small as a microliter (however is not limited to any particular volume) with little difficulty in terms of sample handling. In particular, the probe 30 is suitable for in-situ characterization of a viscoelastic material with minimal damage to the material's structure. The size of the probe 30 can be easily scaled up or down to a size appropriate for a sample to be characterized in a specific application, such that the sample does not need to be contained in any special vessel or container, and can be tested in its natural state and/or environment. Moreover, the probe 30 and system 10 can be used as a portable, handheld unit. This is especially useful for in-vivo characterization, or characterizing toxic materials or materials with limited handling flexibility The probe 30 of the technology described herein has many applications in a diverse range of industries from healthcare and biotechnology (e.g. biomaterial characterization and health diagnostics) to aerospace (material processing). The microrheology probe 30 is capable of characterizing viscoelastic liquids, gels, biological fluids, biological tissues, melt polymers, and elastic solids. Using the micro-probe 30 of the technology described herein, one can estimate the rheological properties (and resulting molecular structure) of a medium such as polymeric coatings as they are applied to the place of interest.

In a preferred configuration, the needle-like probe 30 and system 10 are used for in-vivo characterization of the rheological properties of human body biological fluids and gels as well as elastic solids, and in particular, joint fluids, cartilage, and the vitreous humor of the eye, which are generally inaccessible without surgical approaches. The needle-like probe 30 of the technology described herein is uniquely suitable for evaluation of such fluids, as it is minimally invasive to the surrounding tissue. Such evaluation may be used to assess the presence or the risk of diverse pathologies (including ocular diagnosis). The size of this diameter $\phi$ of the probe (e.g. 20 gauge or more (less than 1 mm), and preferably 25 gauge of more for vitreous humor analysis) is within the range allowed clinical and surgical practices.

Figure 3:
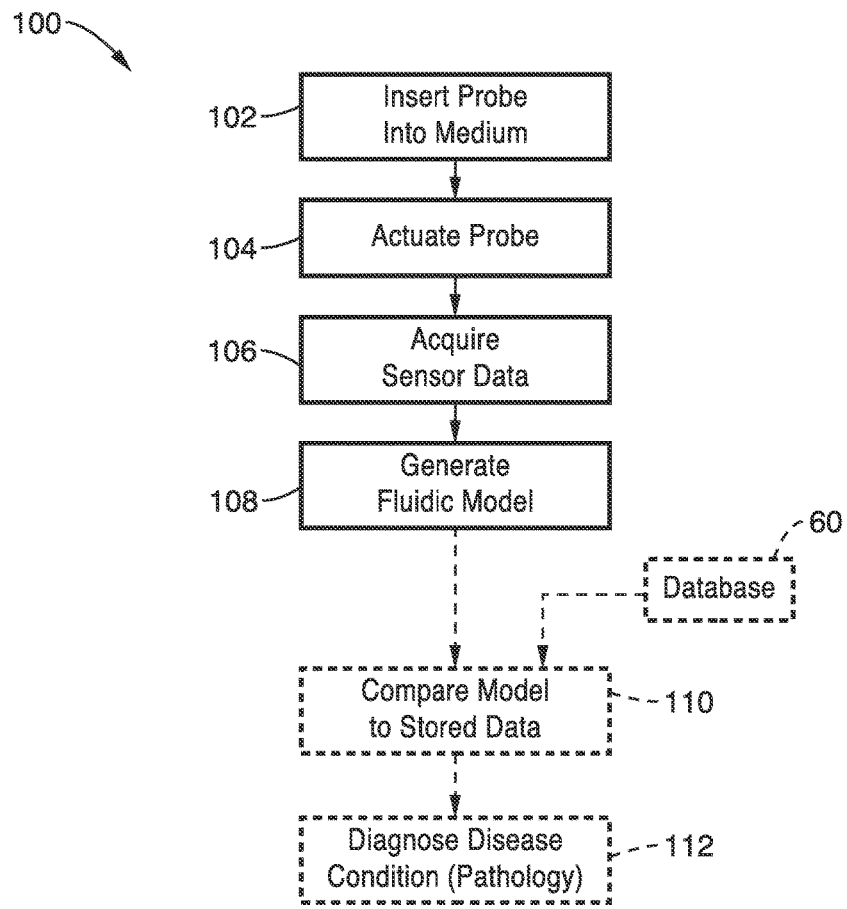
FIG. 3 is a flow diagram of a method for obtaining rheological properties of viscoelastic medium in accordance with the technology described herein.

FIG. 3 illustrates a method 100 for obtaining rheological properties of viscoelastic medium in accordance with the technology described herein.

Figure 5A:
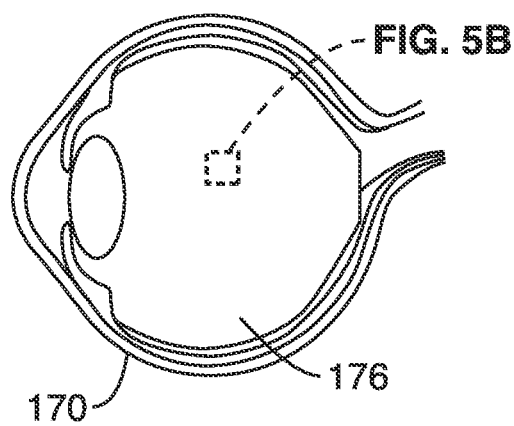
FIG. 5A is a schematic diagram of the human eye and vitreous.

The first step in method 100 is insertion of the probe 30 into the target medium at 102. For in-vivo measurements, the needle-like probe 30 is inserted in the cavity or organ of interest (eye, joint or any other cavity or organ) to directly obtain the viscoelastic properties of the body fluid (such as the vitreous) that correspond to its macromolecular structure. Referring to FIG. 5A, this involves piercing the eye 170 to access the vitreous humor 176 within. Piercing the eye may be accomplished with a sharp-tipped trocar or needle (not shown), within which the probe 30 may then be advanced to access the vitreous 176. In such case, the internal surface of the trocar or probe may be modified with anti-friction means such as a coating or magnetization (not shown) to minimize any alteration of measurements that are induced by the trocar. Alternatively, the distal tip 36 of the probe 30 may be sharpened such that it may be used to pierce the eye 170.

At step 104, the probe actuator 20 is actuated to drive rotational motion of the probe 20. In one embodiment, the actuator 20 rotates the probe 30 with a constant torque (e.g. less than 0.1 mN·m). In such case, the amount of rotational displacement or velocity caused by the target fluid 42 from the rotation of the probe 30 is recorded using a sensor 22 coupled to the actuator 20. Alternatively, the actuator 20 may be operated at a fixed speed, such that the sensor measures changes in the force as a result of the resistance provided by the medium 42. Further alternatives include oscillating stress, strain or the like.

At step 106, the data from the sensor 20 is acquired via computing device 50. Application software 54 then generates a fluidic model 108 based on the acquired sensor data.

Figure 4:
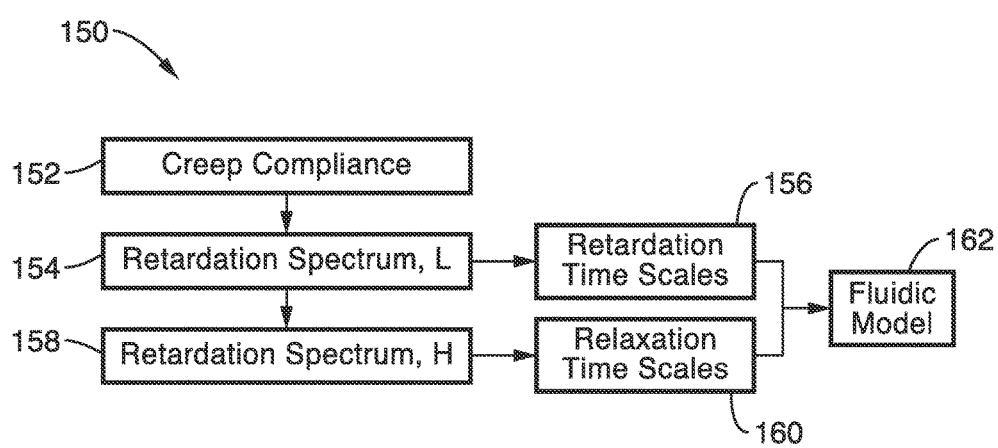
FIG. 4 is a flow diagram of a method for generating a fluidic model according to the method of FIG. 3.

In general, the invented probe can be used to obtain the response of the target fluid 42 (for instance the vitreous humor) to various kinds of time-dependent patterns of stress and strain using appropriate constitutive equations. FIG. 4 illustrates a schematic flow diagram of one method 150 to obtain a fluidic model 162 generated via creep compliance, which can be further used to determine properties such as elasticity and viscosity of the fluid 42. It is appreciated that fluidic modeling method 150 using creep compliance is merely one exemplary method of generating a fluidic model, as the probe 30 can be used to obtain other rheological properties of the target fluid 42, such as, but not limited to, Relaxation Modulus, Complex Modulus, Storage Modulus, Loss Modulus, Complex Compliance, Storage Compliance, Loss Compliance, Equilibrium Modulus, Glass-like modulus, Equilibrium Compliance, Glasslike Compliance, Steady State Compliance, Steady-Flow Viscosity, and Dynamic Viscosity, etc.

Referring back to FIG. 3, stored data from database 60 may be used at step 110 to compare the fluidic model generated at step 108 to reference fluids/materials for further characterization. By acquiring data at step 106 in-vivo, characteristics of human body fluid related diseases and pathologies may further be obtained at step 112.

For example, the probe 30 may be used to diagnose the risk or the presence of a degenerative or pathologic modification of the body fluid 42 related to known or unknown diseases, which occur mostly due to the body fluid's (including the vitreous humor 176) macromolecular organization and viscoelastic properties.

In the ophthalmologic field for instance, method 100 may be used for both early diagnostic and prevention of vitreous related complications. Several ocular pathologies such as retinal tear, rhegmatogenous or tractional retinal detachment, retinal edema, choroidal detachment, vitreous hemorrhage, and glaucoma can arise as a result of vitreous related modification, which occur mostly due to the vitreous humor's macromolecular organization and viscoelastic properties. Knowing such properties allows a surgeon to directly examine the quality of the vitreous and further understand the related pathologies.

In addition, the system 10 and method 100 can be utilized in health care industry both in research and development. More specifically, system 10 and method 100 of the technology described herein may also be used in quantifying the effects of a particular drug or device on the quality of vitreous humor. The needle-like probe 30 of the technology described herein allows for characterization of the viscoelasticity of the vitreous and quantification of viscoelastic changes of the vitreous gel in-situ with minimal damage to the vitreous structure and its surrounding tissues. Therefore, probe 30 can be utilized in characterization of effects of the vitreous related drugs and pharmacologic vitreolysis or early diagnostic and prevention of vitreous related complications.

II. Rheological Modeling Methods

In a preferred method of the technology described herein, the modeling method 150 illustrated in FIG. 4, is used in accordance with step 108 of method 100 (FIG. 3) to model a fluidic behavior of the vitreous gel. It is appreciated that this method, 150, which uses creep compliance measurements, is merely one approach that may be employed, and is illustrated further with respect to FIG. 6 through FIG. 10 for illustrative purpose only. From a single simple creep compliance measurement (step 152), exact relation and time scales may be derived for calculating any other viscoelastic function in shear over sufficiently wide range of time or frequency. Relevant viscoelastic parameters may further be obtained to model dynamic viscoelasticity of vitreous gel. From the measured creep compliance at step 152, retardation and relaxation spectrum were calculated at steps 154 and 158. From those spectrum, relaxation and retardation time scales are obtained at steps 156 and 160 to generate a rheological model at step 162.

Creep compliance, J(t), is calculated according to Eq. 1:

$$J(t) = \frac{\gamma(t)}{\tau_0} \qquad \text{Eq. 1}$$

where $\gamma(t)$ is deformation (strain) and $\tau_0$ is a constant shear stress.

The simplest mechanical model analogous to a viscoelastic system is one spring combined with one dashpot. If the spring and dashpot are in series, the element is called Maxwell; if the spring and dashpot are in parallel, the element is called Voigt. In the Maxwell element, the spring corresponds to a shear rigidity $G_i=1/J_i$ (Pa) and the dashpot to a viscosity $\eta_i$ (Pa·s). Then, the relaxation time of the element is defined as $\tau=\eta_i/G_i$ (s), which is the measure of time required for stress relaxation. The viscoelastic functions derived from Maxwell element are:

$$G(t)=G_i e^{-t/\tau}, \qquad \text{Eq. 2}$$

$$J(t)=J_i+t/\eta_i. \qquad \text{Eq. 3}$$

For the Voigt element, spring and dashpot have the same significance as before, but $\tau=\eta_i/G_i$ (s) is defined as the retardation time, which is the measure of the time required for the extension of the spring to its equilibrium length while retarded by the dashpot. The viscoelastic functions derived from Voigt element are:

$$J(t)=J_i(1-e^{-t/\tau}), \qquad \text{Eq. 4}$$

$$G(t)=G_i. \qquad \text{Eq. 5}$$

A Maxwell element describes a "stress relaxation" experiment, while a Voigt element is suitable to describe "creep compliance." A group of Maxwell elements being parallel represents a discrete spectrum of the relaxation times, where each time $\tau_i$ is associated with a spectral strength $G_i$. If there are n elements then, $$G(t) = \sum_{i=1}^{n} G_i e^{-t/\tau_i}. \qquad \text{Eq. 6}$$

For a viscoelastic solid, at least one relaxation time must be infinite which corresponds to a strength of $G_e$, equilibrium modulus. A group of Voigt elements in series represents a discrete spectrum of retardation times, each associated with a compliance $J_i$. If there are n elements then, $$J(t) = \sum_{i=1}^{n} J_i (1 - e^{-t/\tau_i}). \qquad \text{Eq. 7}$$

In the case of an uncross-linked polymer, a term $t/\eta_o$ must be added (one of the springs has a zero rigidity). Any experimental creep data can be fitted using the retardation spectrum (Eq. 7) with a sufficient number of n. This would determine the spectrum of "line," each with location of $\tau_i$ and intensity of $J_i$. Using certain molecular theories, it is possible to associate these time scales with molecular structure.

More accurate interpretation of the experimental data may be obtained using continuous spectra. If the number of elements in the Maxwell model is increased without limit, a continuous spectrum can be obtained. In a logarithmic expression, the continuous relaxation spectrum is defined as Hd ln τ that is the contribution to rigidity associated with relaxation times, which lie in the range between τ+d ln τ. Therefore the Maxwell elements can be expressed as, $$G(t) = G_e + \int_{\infty}^{\infty} H(\tau) e^{-t/\tau} d \ln \tau. \qquad \text{Eq. 8}$$

The constant $G_e$ is added to represent the viscoelastic solid with $\tau = \infty$. Obviously, for viscoelastic liquids, $G_e = 0$. Plots of H as a function of log τ represent different viscoelastic behavior in a wide time scale range. Their maxima represent concentrations of relaxation processes in certain regions of time scale τ.

Similarly, if the number of elements in Voigt model is increased without limit, a continuous spectrum of retardation times, L, could be obtained from Voigt elements, $$J(t) = J_e + \int_{\infty}^{\infty} L(\tau)(1 - e^{-t/\tau}) d\ln\tau + \frac{t}{\eta_0}. \qquad \text{Eq. 9}$$

When $\tau = 0$ (e.g. viscoelastic liquids), $J_e$ must be added. Plots of L as a function of log τ represent different viscoelastic behavior in a wide time scale range. If one spectrum is known over the entire range of the time scales, another spectrum could be calculated using following expressions, $$L(\tau) = \frac{H(\tau)}{\left[G_e - \int_{\infty}^{\infty} \frac{H(u)}{\tau/u - 1} d\ln u\right]^2 + \pi^2 H(\tau)^2}, \qquad \text{Eq. 10}$$

$$H(\tau) = \frac{L(\tau)}{\left[J_e - \int_{\infty}^{\infty} \frac{L(u)}{1 - u/\tau} d\ln u - \frac{t}{\eta_0}\right]^2 + \pi^2 L(\tau)^2}. \qquad \text{Eq. 11}$$

To solve these equations, $G_e$, $J_e$, and $\eta_o$ must be known. Although Eq. 10 and 11 show that both relaxation and retardation spectrums are interrelated and essentially provide the same information regarding material structure, it is worthwhile to calculate both, because short time scales (contributions to modulus) are relevant in more detail in H, and long time scales (contributions to compliance) are relevant in more detail in L.

Knowing H, several viscoelastic functions could be obtained by summing over all the infinite elements of Maxwell model over the rage frequencies:

$$G' = G_e - \int_{\infty}^{\infty} [H\omega^2\tau^2/(1+\omega^2\tau^2)] d\ln\tau, \qquad \text{Eq. 12}$$

$$G'' = \int_{\infty}^{\infty} [H\omega\tau/(1+\omega^2\tau^2)] d\ln\tau, \qquad \text{Eq. 13}$$

$$\eta' = \int_{\infty}^{\infty} [H\tau/(1+\omega^2\tau^2)] d\ln\tau. \qquad \text{Eq. 14}$$

Similarly, several viscoelastic functions related to L could be obtained by summing over all the infinite elements of Voigt model over the range of frequencies:

$$J' = J_g - \int_{\infty}^{\infty} [L/(1+\omega^2\tau^2)] d\ln\tau, \qquad \text{Eq. 15}$$

$$J'' = \int_{\infty}^{\infty} [L\omega\tau/(1+\omega^2\tau^2)] d\ln\tau, \qquad \text{Eq. 16}$$

$$J_e = \int_{\infty}^{\infty} L d\ln\tau + J_g, \qquad \text{Eq. 17}$$

where $J_g$ is the steady state compliance.

While it is relatively easy to obtain viscoelastic functions from relaxation, H, and retardation, L spectra, obtaining these spectra from a known experimental data is not as simple. Schwarzl and Staverman approximation provides a method to calculate retardation spectrum from a known creep experiment, $$L(\tau) = (d/d \ln t)[J(t) - dJ(t)/d \ln t]|_{t=2\tau}. \qquad \text{Eq. 18}$$

Using Eq. 18, the retardation spectrum could be obtained. However, noises in experimental data results in non-linear values in L when derivatives are taken on J(t). In addition, calculation of the relaxation spectrum using Eq. 11 requires $J_g$ and $\eta_o$. These values can only be obtained using an iterative method to minimize the differences between theoretical and experimental data. A nonlinear regularization method called Tikhonov regularization is used to solve the minimization between theory and experimental data. Using this method, the retardation spectrum is calculated from experimental data of the creep compliance in the corresponding region. This method minimizes the noise of experimental data and estimates the retardation spectrum, L(τ) from the continuous retardation spectrum (Eq. 9) using the following equation:

$$V[f]_\lambda = \sum_{i=1}^{n} \frac{1}{\sigma_i^2} \left( J_i^\sigma - \left( J(t_i) + \sum_{j=1}^{m} a_j b_j(t_i) \right) \right)^2 + \lambda \|L''\|^2 \qquad \text{Eq. 19}$$

where, $J(t_i)$ is Eq. 9, from which, retardation spectrum L is calculated by minimizing the difference between $J(t_i)$ and experimental data $J_i^o$ with errors $\sigma_1, \ldots, \sigma_i$. λ is the regularization parameter and with an appropriate value for this parameter, the first term on the right hand side of Eq. 9 forces the result to be compatible with the experimental data. Also L" is the second derivative of L, which leads to a smooth estimate for the function L.

Referring now to FIG. 5 through FIG. 10, non-linear regularization was performed on the vitreous creep compliance data in order to calculate L and H, and viscoelastic time scales of intact vitreous and chopped vitreous were calculated according the method 150 of FIG. 4.

Figure 5B:
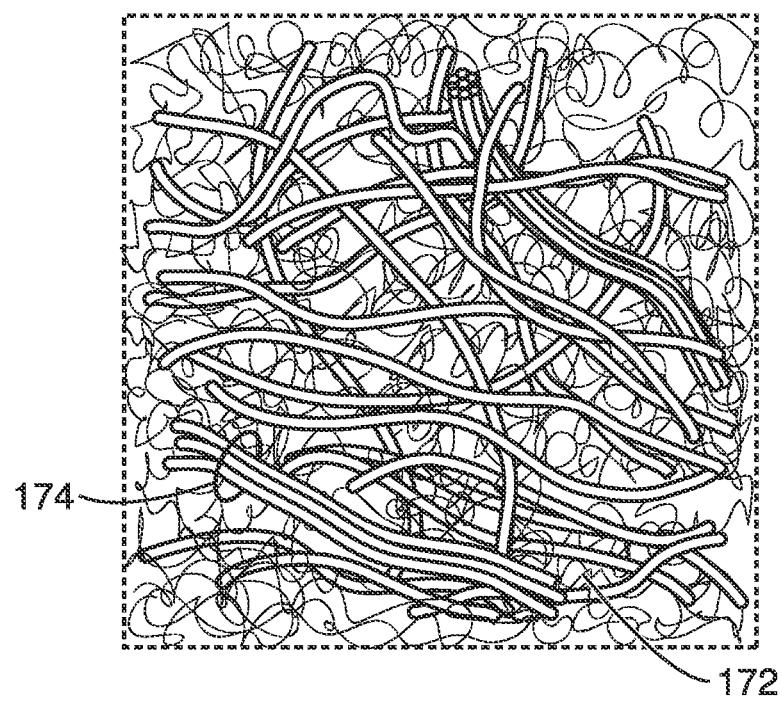
FIG. 5B is an expanded view of the vitreous of FIG. 5A.

Referring to the schematic diagram of the human eye 170 shown in FIG. 5A and FIG. 5B, mechanical properties of vitreous 176 play an important role in normal physiology and several significant human diseases, including rhegmatogenous retinal detachment, proliferative diabetic retinopathy/tractional retinal detachment, and vitreomacular traction/full-thickness macular hole. These mechanical properties are determined by macromolecular structure, namely collagen fibers 174 and glycosaminoglycans 172 such as hyaluronan.

Figure 6A:
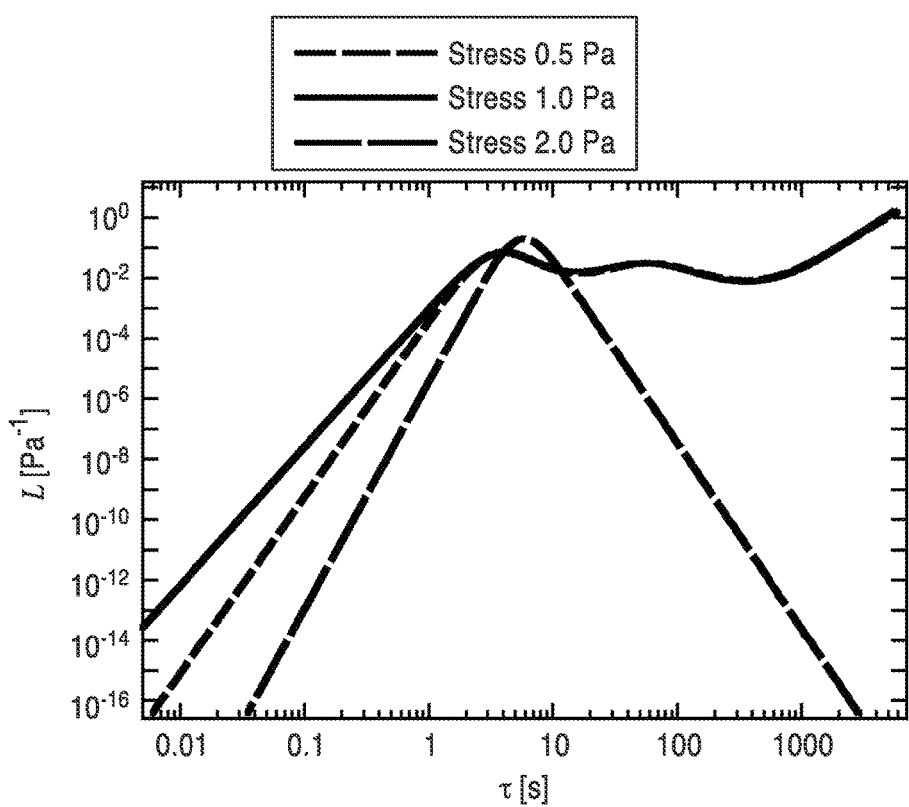
FIG. 6A is a plot illustrating the retardation spectrum of intact vitreous gel for different shear stresses.

FIG. 6A is a plot illustrating retardation spectrum of intact vitreous gel for different shear stresses. The shape of retardation spectrum in FIG. 6A is unique to the macromolecular organization of the vitreous gel. Because vitreous is a viscoelastic gel, the compliance mechanism persists beyond the longest times for which data is available. The results of shear stresses 0.5 and 1 Pa are compatible with this theory. However, for shear stress of 2 Pa, the compliance mechanism was attenuated in long times due to an excessive shear stress.

Figure 6B:
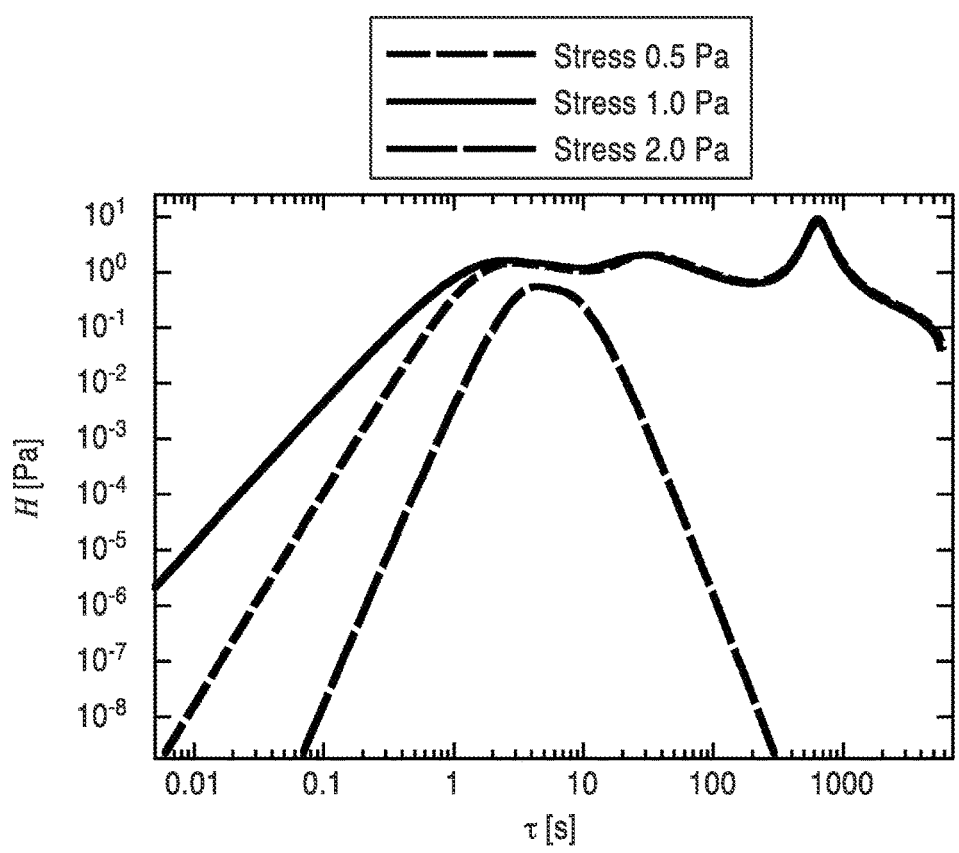
FIG. 6B is a plot showing the relaxation spectrum for intact vitreous calculated from the retardation spectrum of FIG. 6A.

Using Eq. 11 and L, the relaxation spectrum, H, was calculated for intact vitreous gel under different shear stresses (FIG. 6B). Similar to the retardation spectrum, the shape of relaxation spectrum in FIG. 6B is unique to the structure of the vitreous gel. For the viscoelastic solids (e.g.\ vitreous gel), relaxation spectrum, H, attains quite low values at long times. But, there is no evidence showing that it approaches zero, implying that some degree of relaxation continues at long times. Using H, the characteristic zones of the viscoelastic time scales can be identified as: the glassy zone to the left of principle maximum; the transition zone where H drops steeply; the terminal zone when it approaches zero. Retardation spectrum, L, and relaxation spectrum, H are fundamentally interrelated. For example, the plateau or minimum in the spectrum H.

The maximum points in the retardation spectrum and retardation spectrum represent concentrations of retardation and relaxation processes in certain region of time scales, respectively. These time scales are used for dynamic modeling of vitreous gel and fluidic behavior. The summary of retardation and relaxation time scales of vitreous gel obtained from continuous spectrum is provided in Tables \ref{retardmax-intact} and \ref{relaxmax-intact}. Results show that the vitreous gel has two fundamental retardation time scales, $\tau_1$ and $\tau_2$. The first time scale is on the order of 1 second and the second time scale is on the order of 100 seconds. Similarly, relaxation spectra reveal two fundamental relaxation time scales on the order of 100 seconds and 1000 seconds for intact vitreous. These results are consistent with the time scales calculated for vitreous gel in Chapter \ref{Viscoelastic properties of vitreous gel}.

Because chopped vitreous is a very dilute biopolymer solution, measuring complete viscoelastic functions and time scales is extremely difficult. The mathematical algorithm 150 of FIG. 4 was to obtain useful viscoelastic functions and time scales from the measured creep compliance of chopped vitreous. This methodology enabled acquisition of both viscous and elastic behavior of chopped vitreous with relatively high accuracy.

Figure 7A:
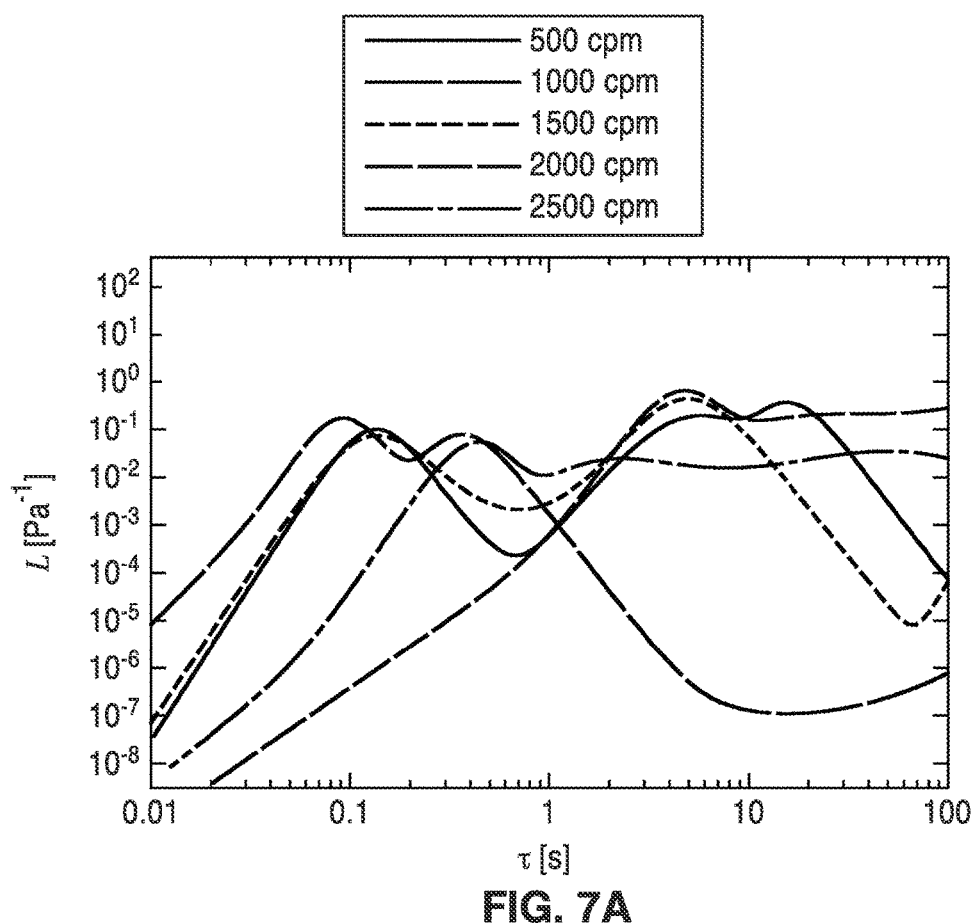
FIG. 7A is a plot of the retardation spectrum for chopped vitreous cut at different cut rates calculated from measured creep compliance using the Tikhonov regularization method.

FIG. 7A illustrates the retardation spectrum calculated for chopped vitreous cut at different cut rates using the methods explained above. As previously explained, the shape of the retardation spectrum in FIG. 7A is unique to the macromolecular organization of the vitreous biopolymeric solution. Chopped vitreous is a diluted, un-crossed viscoelastic liquid and as it is expected, at long times L vanishes when the liquid reaches steady state compliance.

Figure 7B:
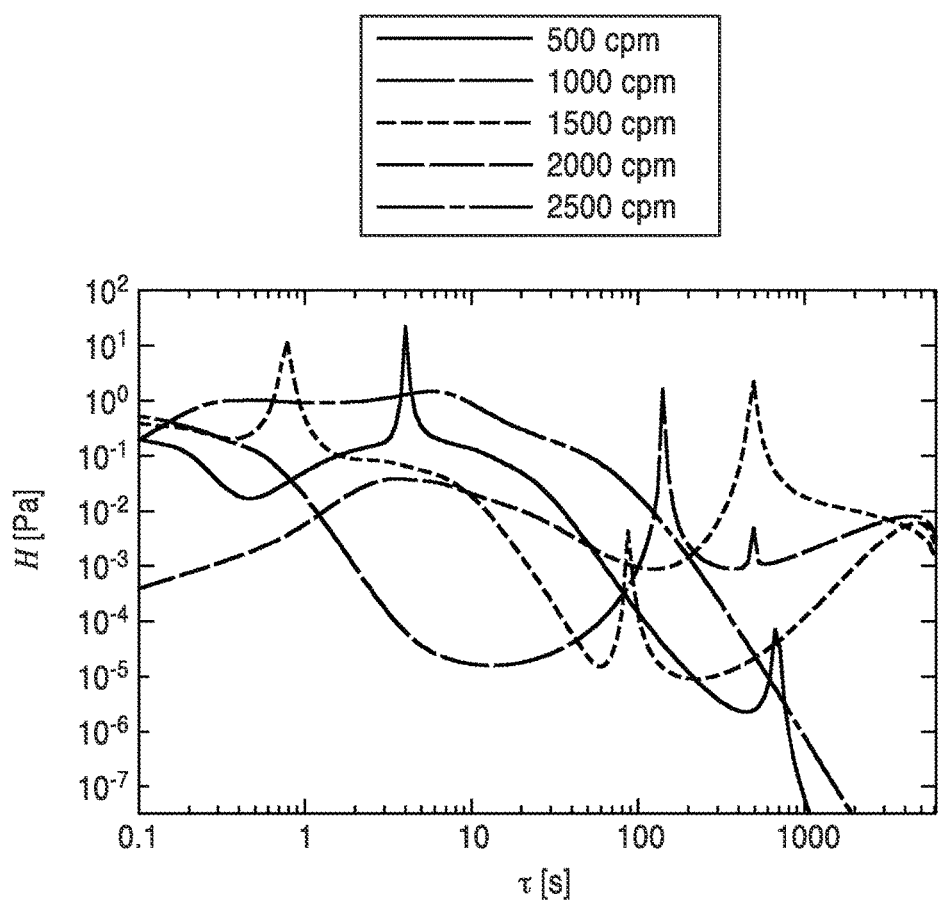
FIG. 7B is a plot of the relaxation spectrum for chopped vitreous cut at different cut rates calculated from the retardation spectrum of FIG. 7A.

Similarly, relaxation spectra was calculated using Eq. 11 and L for chopped vitreous cut at different cut rates (FIG. 7B). Similar to the retardation spectrum, the shape of relaxation spectrum in FIG. 7B is unique to the structure of the vitreous solution. For chopped vitreous, which is an uncross-linked viscoelastic liquid, the relaxation spectrum, H, vanishes when steady-state flow is reached.

Figure 8:
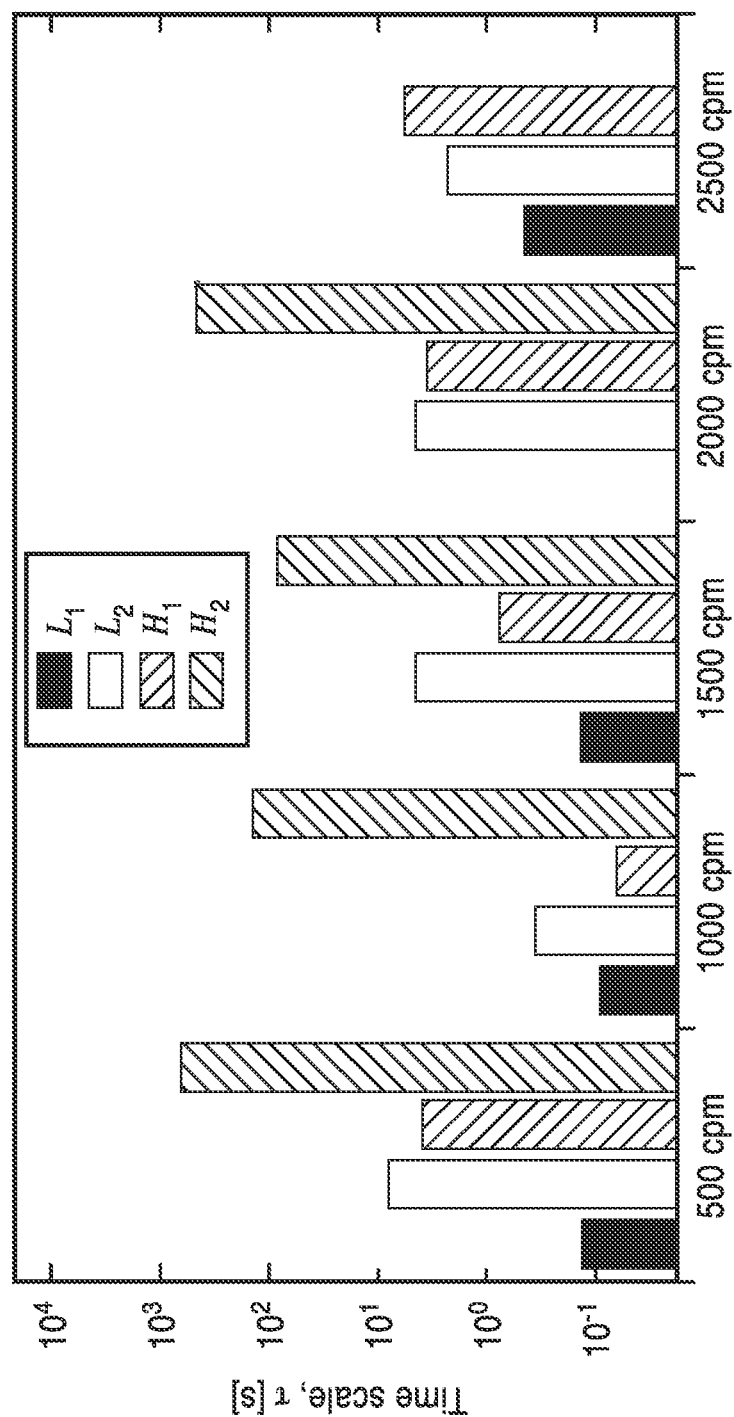
FIG. 8 shows a plot summarizing retardation and relaxation time scales.
Figure 9:
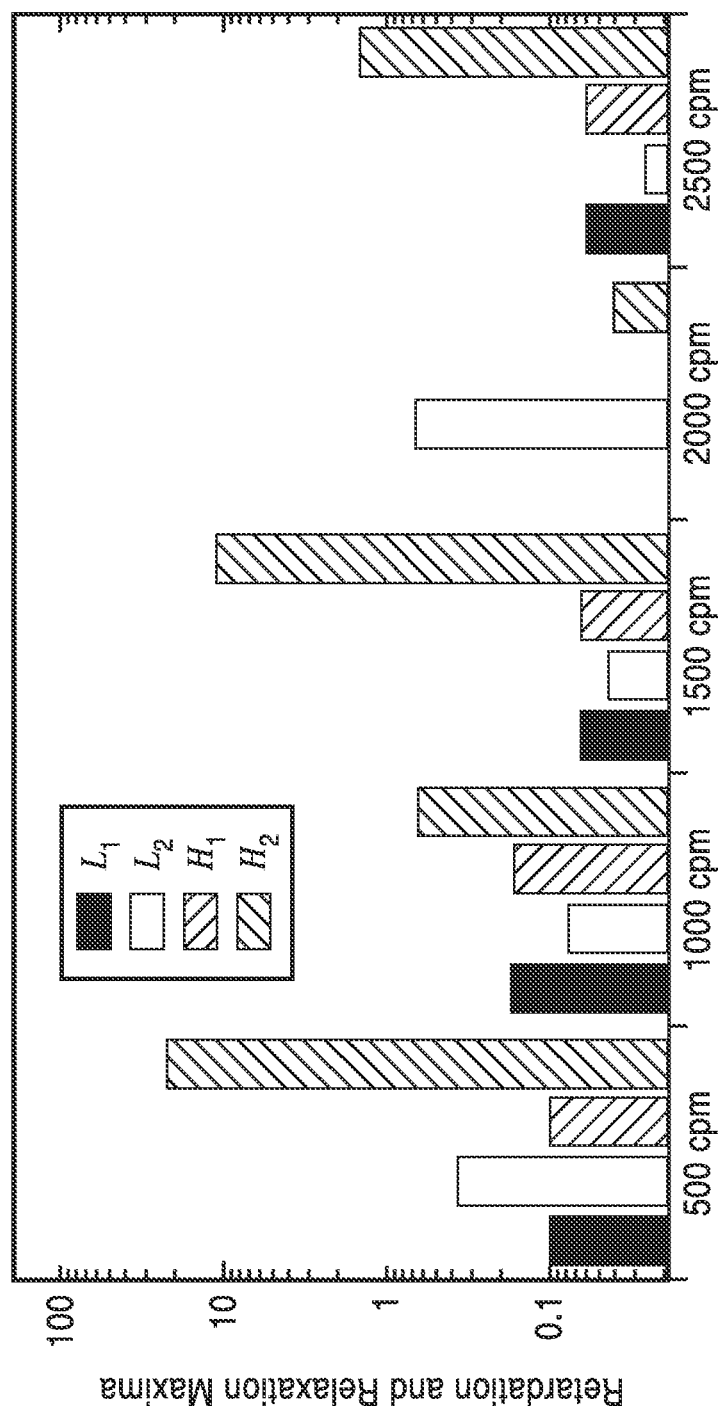
FIG. 9 shows a plot of maxima obtained from the continuous spectrum.

The maximum points in the retardation spectrum and retardation spectrum of chopped vitreous were the concentrations of retardation and relaxation processes. FIGS. 8 and 9 summarize retardation and relaxation time scales and maxima obtained from the continuous spectrum, respectively. Results show that the chopped vitreous has two fundamental retardation time scales and relaxation time scales. The first retardation time scale is on the order of 0.1 second and the second time scale is on the order of 10 seconds. Clearly, retardation mechanism for chopped vitreous was reduced from that of intact vitreous gel (time scales are shorter). The relaxation spectrum reveals two fundamental relaxation time scales on the order of 10 seconds and 100 seconds. Similar to the retardation behavior, relaxation mechanism for chopped vitreous was reduced from that of intact vitreous gel (time scales are shorter).

In most viscoelastic models retardation time scale (associated with viscous behavior) and relaxation time scale (associated with elastic behavior) are the fundamental rheological parameters. It should be noted that because of the retardation or relaxation mechanism corresponding to the shorter time scales that occur first, only these time scales are important for rheological modeling.

The fluidic behavior of the vitreous gel was also modeled using different viscoelastic models to simulate its rheological behavior. Two different cases of intact vitreous gel and chopped vitreous were considered for dynamic modeling. The differences in the viscoelastic behavior of the intact vitreous gel and chopped vitreous were comprehensively studied. It was shown that the vitreous gel is a solid-like viscoelastic substance with a substantial elastic behavior and yield stress.

In contrast, chopped vitreous is a dilute solution of macromolecules that are broken down into small pieces by the vitreous cutter. Both intact vitreous and chopped vitreous are considered to be non-Newtonian fluids, as their rheological properties are directly dependent of flow conditions.

When a non-Newtonian fluid exhibits only fluid-like behavior, it is as a viscous and inelastic fluid and the viscosity of the fluid is a function of shear rate. The viscosity of chopped vitreous decreases monotonically with increasing shear rate. This phenomenon is called shear-thinning or pseudo-plastic. If the elastic behavior of chopped vitreous is neglected, the viscosity can be modeled using a power law.

Both vitreous gel and chopped vitreous exhibit elastic and viscous behavior when subjected to a shear displacement. Therefore, they are visco-elastic fluids. The intact vitreous gel has a longer time scale (1 s) subjected to the immediate elastic response compared to that of the chopped vitreous (0.1 s). Therefore, an appropriate rheological model, which includes both elastic and viscous behavior, must be used to model fluidic behavior of both intact and chopped vitreous. The Giesekus model was used to account for both elastic and viscous behavior.

Chopped vitreous exhibits shear-thinning behavior. A power-law model was used to describe chopped vitreous shear thinning behavior. The power-law model is expressed as, $$\eta = m\dot{\gamma}^{n-1} \qquad \text{Eq. 20}$$

where $\eta$ is the viscosity (Pa·s), and m and n are the consistency index and dimensionless flow behavior index, respectively. Values of m and n are empirical and obtained from experimental data. Shear flow experiments were performed on chopped vitreous cut using 25 gauge open-sky vitrectomy at five cut rates (500, 1000, 1500, 2000, and 2500 cpm).

Figure 10:
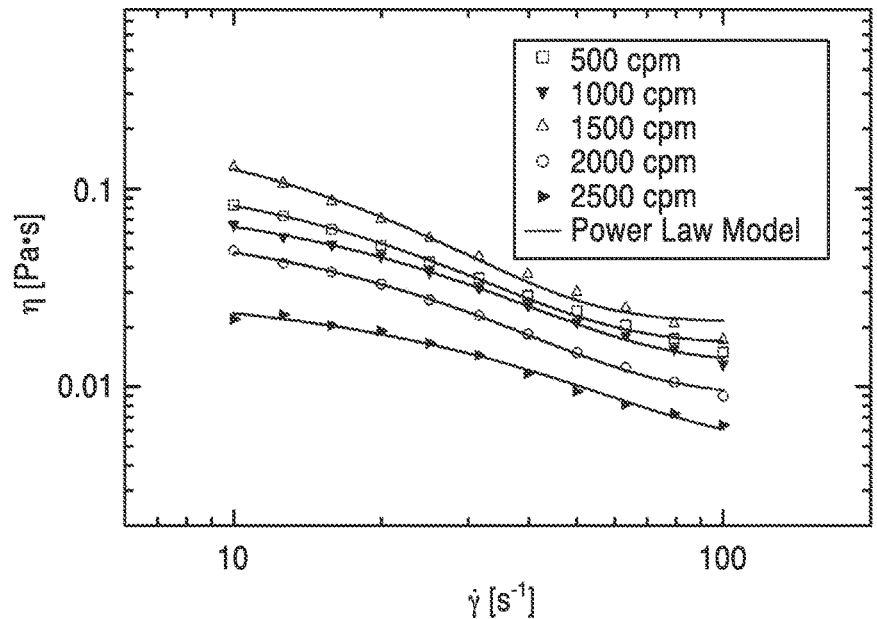
FIG. 10 shows a plot of the power law model applied on viscosity measurement of chopped vitreous as a function of shear rate for different cute rates of 500, 1000, 1500, 2000, and 2500 cpm.

FIG. 10 shows a plot of the power law model applied on viscosity measurement of chopped vitreous as a function of shear rate for different cute rates of 500, 1000, 1500, 2000, and 2500 cpm. Results show a great agreement between experimental data and power law model. Values of flow behavior index, n, were less than 1 for all cut rates implying shear thinning behavior for all the samples cut at different cut rates.

Although power-law provides an insight on shear thinning behavior of chopped vitreous, it does not provide any information on its elastic behavior. The Giesekus model, which models both shear-thinning and elastic behavior, was applied on intact and chopped vitreous. The Giesekus model is mathematically expressed as a superposition of solvent and polymer contribution on shear stress, $\tau_s$ and $\tau_p$:

$$\tau = \tau_s + \tau_p, \qquad \text{Eq. 21}$$

$$\tau_s = -\eta_s \dot{\gamma}, \qquad \text{Eq. 22}$$

$$\tau_p + \lambda_1 \tau_{p(1)} - \alpha \frac{\lambda_1}{\eta_p} \{\tau_p \cdot \tau_p\} = -\eta_p \dot{\gamma}. \qquad \text{Eq. 23}$$

The model contains four parameters: a relaxation time, $\lambda_1$; the solvent and polymer contribution to shear-zero viscosity, $\eta_s$ and $\eta_p$; and the "mobility factor," $\alpha$. The value $\alpha$ is associated with Brownian motion and/or hydrodynamic drag on the polymer molecules, and it is usually required to be $0 < \alpha < 1/2$. By combining Eq. 21 and Eq. 22, and replacing $\tau_p$ in Eq. 23, a single constitutive equation for Giesekus model is obtained:

$$\tau + \lambda_1 \tau_{p(1)} - \alpha \frac{\lambda_1}{\eta_o} \{\tau \cdot \tau\} - \qquad \text{Eq. 24}$$

$$a\lambda_2\{\gamma_{(1)} \cdot \tau + \tau \cdot \gamma_{(1)}\} = -\eta_o \left[ \gamma_{(1)} + \lambda_2 \gamma_{(2)} - a \frac{\lambda_2^2}{\lambda_1} \{\gamma_{(1)} \cdot \gamma_{(1)}\} \right]$$

where $\eta_o$ is a shear-zero viscosity, $\lambda_2$ is the retardation time scale, and a is a modified mobility.

All these parameters can be also written as:

$$\eta_o = \eta_s + \eta_p. \qquad \text{Eq. 25}$$

$$\lambda_2 = \lambda_1 \frac{\eta_s}{\eta_s + \eta_p}, \qquad \text{Eq. 26}$$

$$a = \alpha \frac{(\eta_s + \eta_p)}{\eta_p}. \qquad \text{Eq. 27}$$

When a nonlinear stress term (i.e.\ shear thinning behavior) in the Giesekus model is neglected, the model is reduced to an Oldroyd B model, which is widely used to model fluid dynamic of various dilute polymer solutions. Because vitreous gel does not have shear thinning behavior, essentially either the Giesekus model or the Oldroyd B model could be used to model its fluid flow. In order to compare the model with the experiential data, we used the solution of the Giesekus model for a steady shear flow to calculate viscosity as a function shear rate:

$$\frac{\eta}{\eta_o} = \frac{\lambda_2}{\lambda_1} + \left(1 - \frac{\lambda_2}{\lambda_1}\right) \frac{(1-f)^2}{1 + (1 - 2\alpha)f}, \qquad \text{Eq. 28}$$

where, $$f = \frac{1-\chi}{1 + (1 - 2\alpha)\chi}, \qquad \text{Eq. 29}$$

and, $$\chi^2 = \frac{(1 + 16\alpha(1-\alpha)(\lambda_1 \dot{\gamma})^2)^{1/2} - 1}{8\alpha(1-\alpha)(\lambda_1 \dot{\gamma})^2}. \qquad \text{Eq. 30}$$

Figure 11:
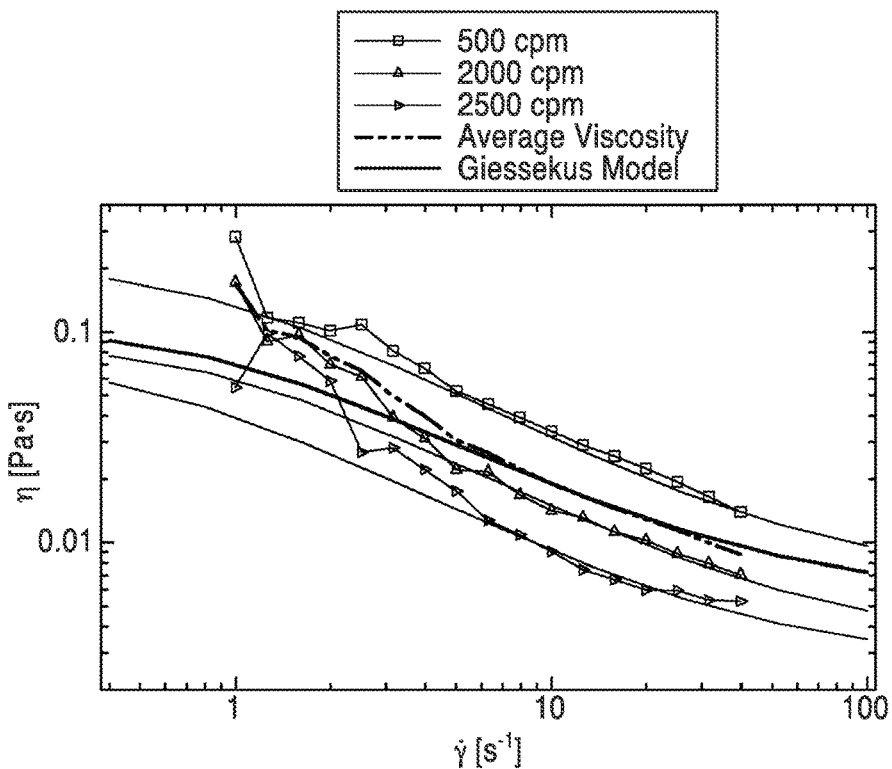
FIG. 11 shows a plot of the Giesekus model applied on viscosity measurement of chopped vitreous as a function of shear rate for different cute rates of 500, 2000, and 2500 cpm.

FIG. 11 shows a plot of the Giesekus model applied on viscosity measurement of chopped vitreous as a function of shear rate for different cute rates of 500, 2000, and 2500 cpm. Results show a great agreement between experimental data and Giesekus model.

III. Mechanopathology of the Vitreous Gel

Tests were conducted to correlate the structure and viscoelastic properties of the vitreous humor (e.g. model generated in step 108 of method 100) to vitreous-related pathologies (e.g. for diagnosis step 112 of method 100). The general premise is that the viscoelastic properties of vitreous humor 176 are determined by its molecular structure (e.g. collagen fibrils 174, hyaluronan 172), which changes depending on the eye condition. Therefore, the measured viscoelastic properties of the vitreous humor can be used to directly detect early stages of eye diseases. Furthermore, the knowledge of such properties for a particular patient can help in optimizing both drug delivery techniques and surgical procedures. The rationale for the methodology presented here is derived from findings of this study which clearly tie the viscoelastic properties of the vitreous to its macromolecule structure. As a result, the following hypotheses were established:

1. The viscoelastic properties of the vitreous extracted by regular vitrectomy procedure contains information of macromolecule structure of intact vitreous. Such information is projected in the viscosity and elasticity of the chopped vitreous that is tied to the concentration of the collagen structure. For example, if collagen fibers in certain diseases become thicker and more concentrated, consequently the viscosity of the chopped vitreous becomes higher.

Chopped vitreous can be obtained by vitrectomy, and the viscoelasticity of the chopped vitreous in long-term, time-dependent rheology tests can be measured. If we look at one strand of the vitreous gel that undergoes the vitrectomy cutter; it is cut into n segments in a finite time with the same size and rheological properties. If the creep compliance of each segment is $J_n$, then it is a valid assumption that $J_n = J_{gel}$. In other words, the bulk rheological properties of each segment is the same as those of original intact vitreous. Chopped vitreous after vitrectomy consists of a number of segments with the compliance of $J_n$ in a fluid solution. Therefore, the rheological properties (such as creep compliance) of the solution is a function of that of each segment, $$J_{chopped} = f(J_n) \qquad \text{Eq. 31}$$

where f is a nonlinear function of each segment's compliance. Substituting $J_n$ with compliance of whole vitreous gel, $J_{gel}$, we have:

$$J_{chopped} = f(J_{gel}). \qquad \text{Eq. 32}$$

Therefore, compliance of the chopped vitreous is a function of the compliance of the intact vitreous gel. Here, we are not interested in finding the function f. We simply use this argument to show that any elastic and viscous behavior that we observe in the chopped vitreous is a unique signature of elastic and viscous behavior of the intact vitreous before vitrectomy. As a result, plateau creep compliance of chopped vitreous, $J_N$, and steady-state viscosity, $\eta_s$ are the qualitative measure of the viscoelasticity of original vitreous gel before vitrectomy.

2. The creep compliance of the vitreous gel, which is unique to its macromolecular structure, is directly correlated to the pathological condition of the eye. By compiling a database 60 of creep compliance of the chopped vitreous obtained from patients with different age, sex, and eye conditions, we can investigate the correlation between vitreous rheology and ocular pathologies.

In order to realize these assumptions and hypothesis, the following experimental considerations were taken:

(a) Undiluted vitreous sample was collected in a similar vitrectomy fashion in terms of method, gauge size, cute rate, and vacuum pressure. In order to obtain an undiluted sample, air-infusion was used and a 1 cc vitreous sample was. Samples were collected at the boundary of air and vitreous gel inside eye cavity. In order to isolate the effect of cutting speed, suction pressure and the duty cycle of the cutter device on the rheology of extracted vitreous, 23 gauge vitrectomy with 2500 cpm and 500 mmHg vacuum was used in each surgery.

A stress-controlled shear rheometer (AR-2000, TA Instruments) with 20 mm parallel disc geometry was used to measure the rheological properties. The parallel discs were covered with 600-grit silicon carbide sandpaper to minimize the slippage of the sample. In order to minimize the effect of water evaporation and liquid loss, a solvent trap sealed with vacuum oil was used to enclose the sample. All the experiments were done with zero normal force on the samples and at a temperature of 37° C.

Viscosity experiments were performed on the vitreous humor with constant shear rate. The viscosity, $\eta(\dot{\gamma})$, was calculated as $$\eta(\dot{\gamma}) = \frac{\tau}{\dot{\gamma}_0} \qquad \text{Eq. 33}$$

where $\tau$ is shear stress and $\dot{\gamma}_0$ is a constant shear rate.

(b) Samples were tested within 1 hour of extraction to eliminate the effects of sample degradation. Creep compliance of each sample was obtained.

(c) A comprehensive database 60 containing patient's age, sex, eye conditions, and creep compliance of each specimen was established. Using this database, proposed correlation was evaluated by directly tying pathology to the rheology of the extracted vitreous humor.

a. Vitreous Related Pathologies

Many vitreo-retinal pathologic features are related to the vitreous rheology and in the severe cases, require surgical intervention. For example, the process of vitreous liquefaction can cause posterior vitreous detachment that consequently causes retinal tear, retinal detachment, vitreomacular traction syndrome, epiretinal membrane, and macular hole. Clinical observations show that all of these retinal conditions have a peak age of incidence after 50 years which is close to the peak age of posterior vitreous separation. Therefore, the liquefaction of the vitreous gel could be a fundamental cause of common retina disorders. In addition, vitreous rheology could be related to other ocular complications such as nuclear sclerotic cataract.

Age-related liquefaction: The human vitreous experiences an unavoidable process of liquefaction (or syneresis) where gel volume decreases and liquid volume increases with aging. Previous studies showed that around 20% of the vitreous volume is liquid by 14-18 years of age. After the age of 45-50, there is a significant increase in liquid volume which does not occur uniformly within vitreous cavity. Pockets of liquid usually form and enlarge in the central vitreous and by the age of 80-90 years, occupying more than half of the vitreous body. The mechanism of the liquefaction is a gradual and progressive aggregation of the collagen fibrils 174 that provide an empty space for liquid vitreous 176 to fill. The nature of liquefaction is poorly understood. It was shown that the loss of type IX collagen may be responsible for the liquefaction in which the extra surface exposure of type II collagen increases propensity towards fusion of adjacent fibrils. Liquefaction may also result from changes in HA-collagen interaction in which a change in the conformational state of HA molecules causes cross-linking of collagen molecules.

Posterior Vitreous Detachment (PVD): Posterior vitreous detachment (PVD) is a separation of the posterior vitreous cortex from the ILL of the retina. PVD is the most common event occurring as a result of age-related vitreous degeneration. PVD is associated with the weakening of the vitreous cortex-ILL adhesion in conjunction with liquefaction of the vitreous body. Complications arise when dissolution of the vitreous cortex-ILL adhesion at the posterior segment allows liquid vitreous to enter the retrocortical space. With eye movements, liquid vitreous shear stresses dissect a plane between the vitreous cortex and the ILL, leading to complications such as retina tear, and rhegmatogenous retinal detachment (RRD).

Tractional Retinal Detachment (TRD): Tractional retinal detachment (TRD) is a retinal detachment caused by pulling on the retina. In this study, all TRD cases were originated from diabetic pathologies. Elevated glucose causes blood vessel endothelial damage, which develops ischemia. Ischemic tissue releases vascular endothelial growth factor (VEGF), which causes new vessel formation (i.e. neovascularization). Neovascularization takes the form of fronds of vessels growing from the retinal surface into the vitreous, using the vitreous as a scaffold. These fronds of vessels also have porous tissue and are called "brovascular", which can retract and pull on the retina.

Proliferative Diabetic Retinopathy/Vitreous Hemorrhage (PDR/VH): Proliferative diabetic retinopathy (PDR) is caused by changes in the blood vessels of the retina especially the growth of new blood vessels. These blood vessels are abnormal and fragile by nature and grow along the retina and into the vitreous. Complications arise when they leak blood and cause severe vision loss. Presence of blood in the vitreous results in several changes like vitreous hemorrhage (VH) that cannot be always clinically observed as the posterior eye is obscured by the blood. Experimental studies show that vitreous liquefaction (decrease on viscosity) begins during the first week of vitreous hemorrhage.

Rhegmatogenous Retinal Detachment (RRD): Rhegmatogenous retinal detachment (RTD) is a retinal detachment caused by a tear in the retina. The most typical underlying cause is a posterior vitreous detachment from vitreous liquefaction. Starting in childhood, there are areas of vitreous that become liquified. These small lakes of liquified vitreous within the body of the vitreous gel are called bursae. With age, these bursae become larger. Eventually, if a large bursae comes in contact with the retina, the vitreous liquid in the bursae dissects between the retina and the posterior face of the vitreous body. As the liquid vitreous dissects more and more anteriorly, the vitreous body is peeled from the retina and moves anteriorly. This process is limited by the very strong adhesions of vitreous/retina at the ora serrata called vitreous base. As the vitreous is peeled from the retina, in a presence of strong adhesion, there could be a tear in the retina. The liquified vitreous can pass through the tear and cause a retinal detachment.

Vitreomacular Traction (VMT): During a posterior vitreous detachment, there is an area of abnormally strong adhesion between the posterior vitreous face and the macula (the part of the retina responsible for central vision). The vitreous pulls on the macula and causes vitreomacular traction (VMT).

Full-thickness Macular Hole (FTMH): Full-thickness macular hole (FTMH) is similar to VMT, except that the traction causes a retinal hole.

Epiretinal Membrane (ERM): Epiretinal Membrane (ERM) is the condition associated with cell invasion in vitreous and often arises from cell proliferation at or near optic disc. The pathogenesis of epiretinal membrane is not well understood. However, studies show that ERM likely develop during PVD.

Nuclear Sclerotic Cataract: Recent studies show that the vitreous degeneration and the process of liquefaction was linearly associated with development of nuclear sclerotic cataract. In other words, eyes with nuclear sclerotic cataract show faster vitreous degeneration.

b. Correlation Between Vitreous Viscoelasticity and Disease States

Vitreous from 65 eyes were collected during routine surgeries and a complete data set for 55 and 27 eyes was established for compliance and viscosity data, respectively. Also, compliance and viscosity of the patients with phakic (number of cases, n=26) and pseudo/aphakic (n=29), diabedic (n=16) and nodiabetic (n=39), no diabetic retinopathy (n=45) and proliferative diabetic retinopathy (n=10), any tractional diseases (VMT, FTMH, TRD, and RRD, n=19) and no tractional diseases (n=36) were statistically compared.

Most of the patients in this study were older than 50 years. Results show that plateau compliance varies from 14 to 244 $Pa^{-1}$ and viscosity varies from 0.004 to 0.05 Pa·s. There was no relationship observed between patient age and compliance or viscosity for the population that was tested.

Figure 12:
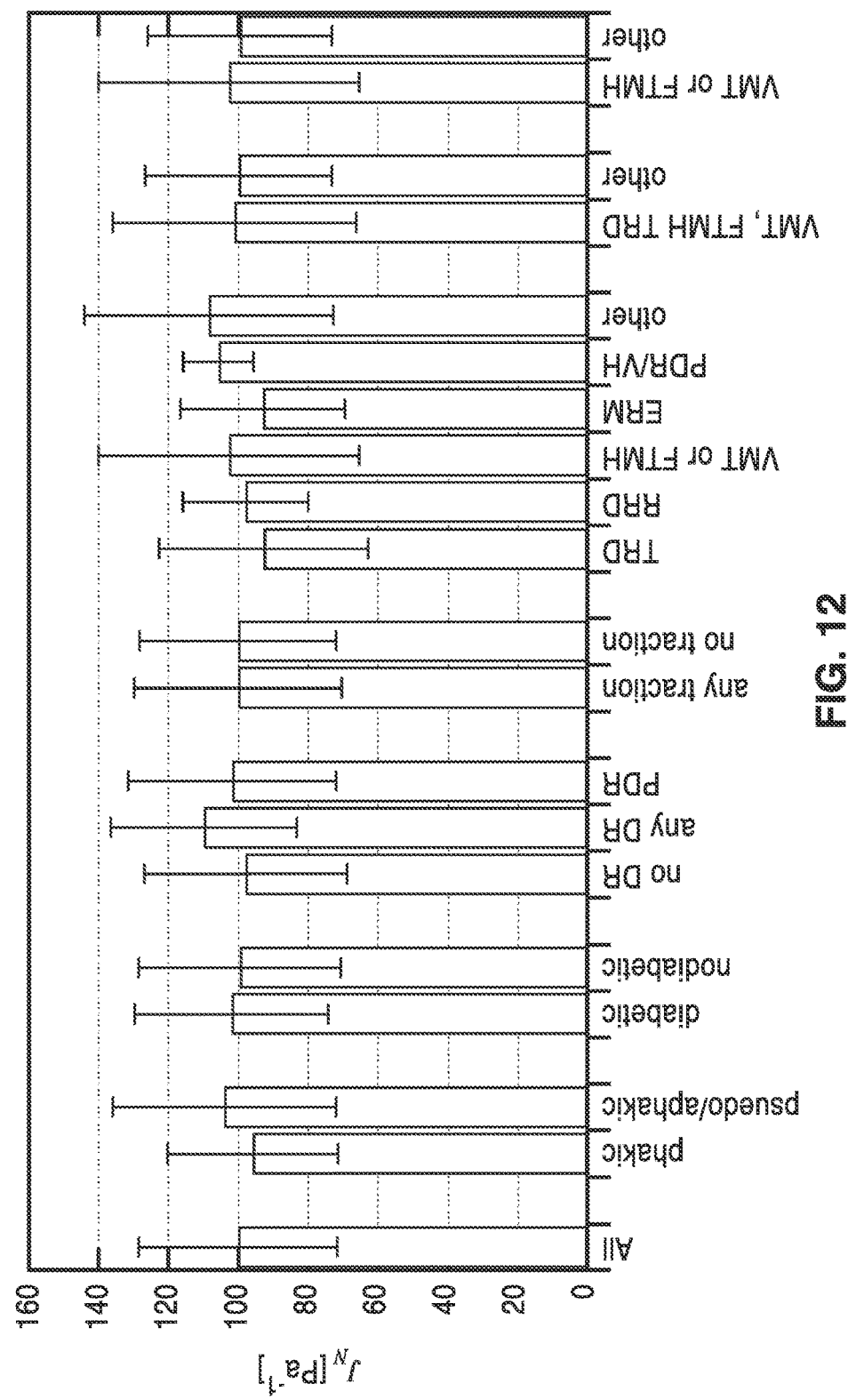
FIG. 12 shows average plateau compliance of the chopped vitreous of patients with different diseases.

The average plateau compliances of the chopped vitreous of patients with different diseases are shown in FIG. 12. The average chopped vitreous compliance is 100.2±28.4 $Pa^{-1}$. No statistically significant difference was found between the compliances of diseases.

Figure 13:
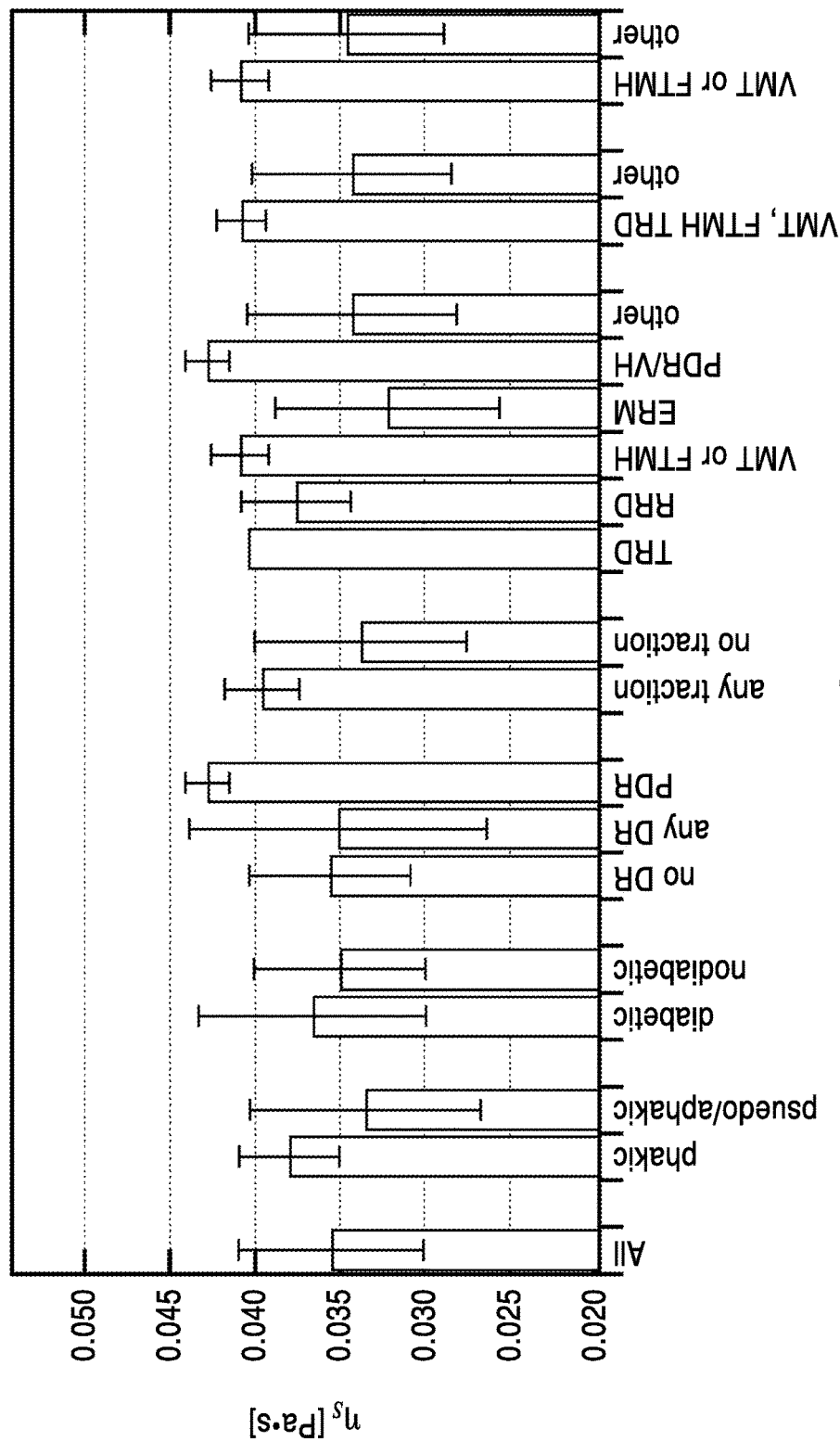
FIG. 13 shows average viscosities of the chopped vitreous of patients with different diseases.

The average viscosities of the chopped vitreous of patients with different diseases are shown in FIG. 13. The average chopped vitreous viscosity is 0.035±0.005 $Pa^{-1}$. Results show that average viscosity of chopped vitreous of phakic patients are higher than that of pseudo/aphakic patients (P=0.262). There is no significant difference between chopped vitreous viscosity of diabetic and nodiabetic patients (P=0.7734). The average viscosity of chopped vitreous in proliferative diabetic retinopathy patients is higher than that of any/no diabetic retinopathy (P=0.0148). Also, results show that chopped vitreous of the patients with tractional diseases have the higher average viscosity than those with no tractional diseases (P=0.0922). It was found that PDR/VH chopped vitreous has the highest average viscosity while ERM chopped vitreous has the lowest average viscosity (P=0.4888). In addition, we compared the viscosity of chopped vitreous with VMT, FTH, and TRD (tractional group) with others and we found that average viscosity is higher for the tractional group (P=0.0324). Also, the average of viscosity of chopped vitreous for patients with VMT or FTMH is higher than the rest (P=0.045). Analyses of presence of diabetes without regard to retinal disease, and other vitreoretinal pathologies did not reveal statistically significant differences.

In conclusion, the value of plateau compliance of chopped vitreous is approximately proportional to the length of each vitreous segment, whereas the viscosity is proportional to the thickness of the vitreous fibers. The plateau compliance is an indication of the quality of the vitreous segment after cut and it is function of cut rates. Whereas, viscosity it is a function of the fiber thickness and concentration (is not a function cut rates and vitrectomy settings). In this study, the vitreous extraction (vitrectomy) was performed with a consistent cut rate and vacuum for all cases. As it was expected, only viscosity of chopped vitreous changed as a result of ocular diseases and compliance remained constant. Results of this study suggest that viscosity of vitreous of patients with tractional diseases are higher. The hypothesis that arises from this observation is that the fiber aggregation for such diseases is higher which causes stronger traction and more dramatic complications. When comparing patient with different age, we did not observe any relationship between patient age and compliance or viscosity for the population that was tested. Although age related fiber aggregation may locally increase vitreous viscosity and cause vitreous related complication, age alone was never the reason for vitrectomy of population that was tested. Therefore, the pathologies that were the reason for vitrectomy in the first place obscured the effect of age.

The results of these studies provide a correlation between vitreous rheological properties and pathological conditions (i.e. mechanopathology) that that may be used in step 112 of method 100 (FIG. 3) to illuminate disease pathogenesis, optimize surgical technique, and target drug delivery to the vitreoretinal compartment. It was shown that a direct link between the viscoelastic properties of the vitreous and number of ocular diseases and pathologies exists. Thus, method 100 may be used to provide early diagnosis of eye pathology caused by mechanical and viscoelastic properties of vitreous gel.

It is appreciated that the above studies were conducted on chopped vitreous conducted with a macrorheology probe. While the in-vivo data acquisition (step 106 of method 100) of whole vitreous using the needle-like probe 30 of the technology described herein is likely to generate significantly different data, it is expected that there will be a correlation between the distinct datasets that will still provide characterization of the pathology or other useful characteristics of the anatomy. Nonetheless, database 60 may comprise data from in-vivo data of un-chopped vitreous as acquired by probe 30 to be used alternatively with, or in combination with, the cut vitreous data.

IV. In-Vivo Characterization of Vitreous Biomechanics

The main challenge to characterize viscoelastic properties of the vitreous gel is that its structure is extremely fragile in nature.

In a preferred embodiment, the cylindrical micro-probe 30 (FIG. 2) of the technology described herein is used to obtain the real-time rheological properties of viscoelastic materials. This probe 30 can be used for small sample volumes, which do not need to be contained in a secondary container for measurements. The probe 30 is directly inserted into the sample or tissue for in situ characterization of a viscoelastic material with minimal damage to the material's structure. The probe 30 of the technology described herein fills the gap between conventional rheology techniques that need large amount of samples for measurements, and microrheology techniques that measure only local properties.

The performance of the microrheology probe 30 of the technology described herein was experimentally investigated. The probe 30 was attached to an AR2000 rheometer to provide constant torque and measure the deformation during the creep test. The hypothesis that the performance of the probe is independent of the container's size was experimentally verified by analyzing creep compliance of Oligomer in containers with various sizes (2, 4, and 6 cm in diameter). A constant stress of 3.6 Pa was applied and the deformation was monitored as a function of time. The creep compliance was then calculated. The results of these different tests confirmed that the measurements of the probe 30 are in fact independent of the container's size and shape.

Figure 14:
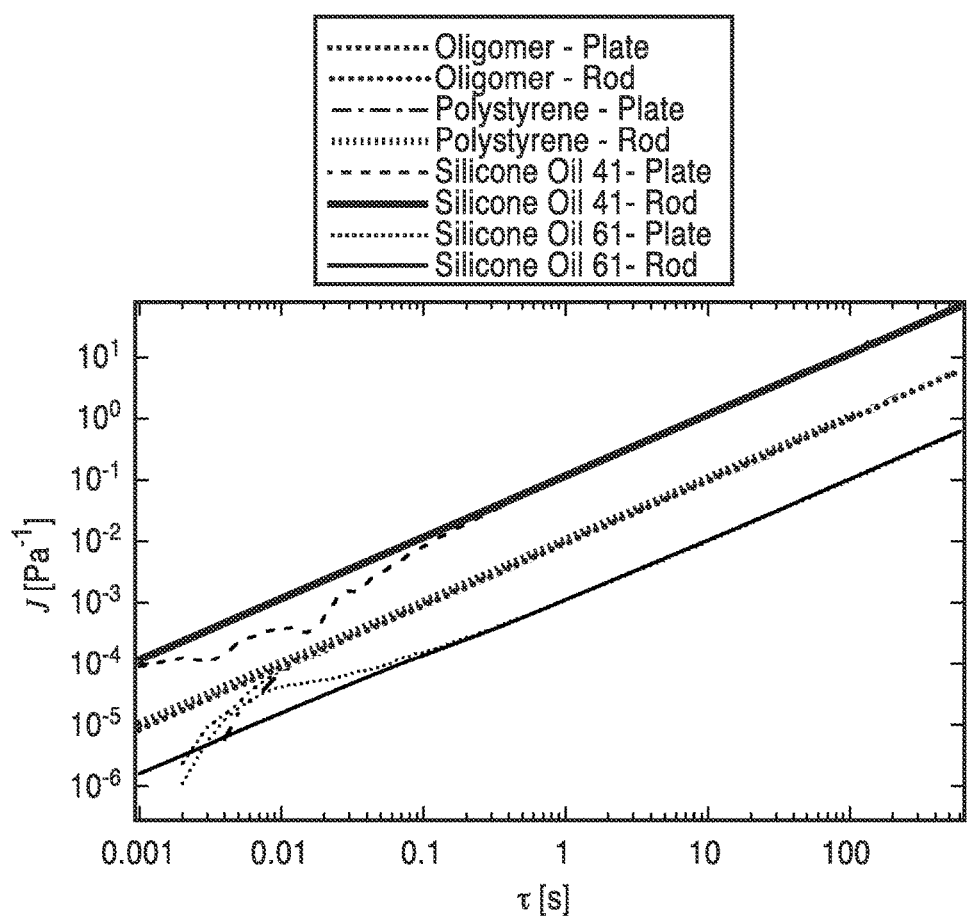
FIG. 14 shows a plot illustrating the comparison between measurements obtained using the rheology rod of the technology described herein and a conventional parallel plate rheometer.

In one experiment, the creep compliance of four different liquids: Oligomer, Polystyrene 0.25, Silicone Oil 41, and Silicone Oil 61, were measured using the rheology rod 30. FIG. 14 illustrates the comparison between the measurements obtained using the rheology rod 30 of the technology described herein and parallel plate rheometer. The values of viscosities were then obtained by measuring the slope of the compliance at long times. Table 1 provides the viscosities calculated from: creep compliance measured using parallel plate ($\eta_{plate}$), creep compliance measured using the rheology rod ($\eta_{rod}$), and flow shear rate experiment using parallel plate ($\eta_{flow}$). Results show that values are similar and in the same order of magnitude for different measurement techniques. Therefore, the rod 30 is suitable for measuring creep compliance of viscoelastic liquids in a wide range of viscosities.

Figure 15:
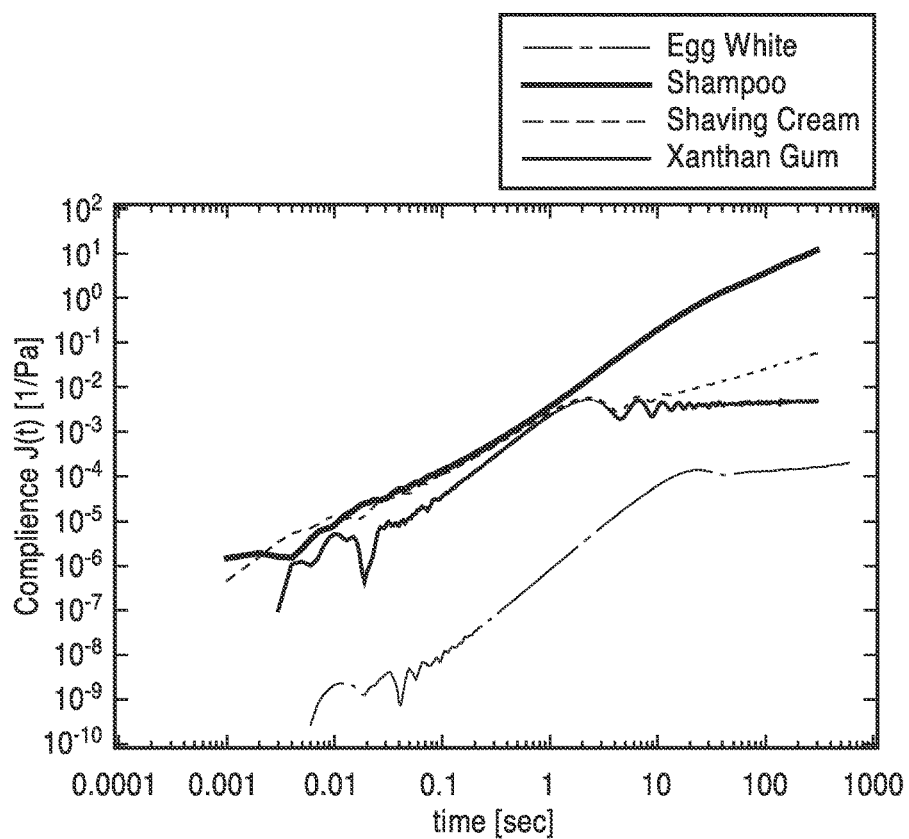
FIG. 15 shows a plot illustrating creep compliance measurements of egg white, shampoo, shaving cream, and xanthan gum materials using the micro-probe of the technology described herein.

A second test was conducted using the same test setup of rod 30 with different mediums (e.g. egg white, shampoo, shaving cream, and xanthan gum). FIG. 15 shows a plot of the measured creep compliance of these various mediums.

The in-vivo creep compliance of the vitreous gel was obtained using the rheology probe 30 shown in FIG. 2. A 1.5 mm diameter incision was created in Sclera of porcine eye at 2 mm distance of the cornea. The tip of the probe (7 mm in length) was directly inserted in the vitreous.

Figure 16:
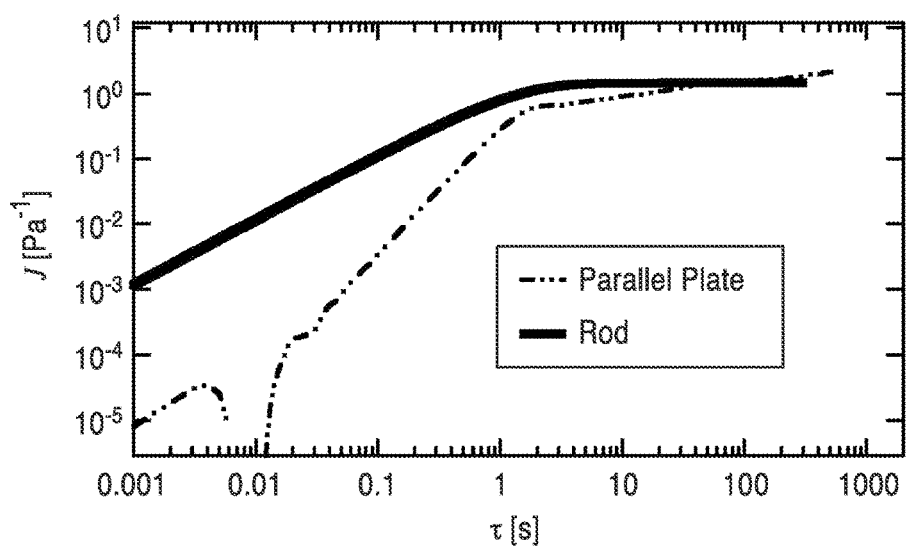
FIG. 16 shows the comparison between the creep compliance of the vitreous obtained using the probe of the technology described herein and conventional a parallel plate.

A constant torque of 0.1 mN·m in the finite time of 600 seconds was applied to the probe 30 using the rheometer's actuator 20. The amount of rotational displacement was recorded and creep compliance was calculated. FIG. 16 shows the comparison between the creep compliance of the vitreous obtained using the probe 30 and conventional a parallel plate. Results show a similar behavior and associated time scales for creep compliances in both cases. In addition, steady state compliances obtained using both techniques are in the same order of magnitude.

The significant aspect of the rheology probe 30 is its small size that permits bulk characterization with minimal damage to the structure of the material. Therefore, it is possible to quantify viscoelastic changes in fragile material such as vitreous gel when it is incubated over time and liquefied in a process of vitreous liquefaction or pharmacologic vitreolysis.

In conclusion, results show that this technique has enough accuracy for analyzing small changes in the vitreous viscoelastic properties. Therefore, the probe 30 can be used for both characterization of effects of the vitreous related drugs and pharmacologic vitreolysis or early diagnostic and prevention of vitreous related complications. In addition, the probe is suitable for in-situ, real time characterization of other viscoelastic material with limited handling. The probe can be used in a portable system and the size of the probe can be easily scaled up or down to an appropriate size for a sample to be characterized in a specific application.

Embodiments of the technology described herein may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means. Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A system for obtaining rheological properties of viscoelastic medium, the system comprising: a needle-like probe having a distal and a proximal end; a rotational actuator; a sensor coupled to the rotational actuator; the proximal end of the probe configured for attachment to the rotational actuator; the distal proximal end of the probe having a roughened outer circumferential surface extending axially along at least a portion of the distal end; wherein the roughed distal end of the probe is configured to be disposed within the viscoelastic medium; and wherein the sensor is configured to obtain measurements corresponding rotation of the probe within the viscoelastic medium.

2. The system of any of the proceeding embodiments, wherein the roughed surface is configured to minimize slippage of the probe with respect to the viscoelastic medium when the probe is rotating within the medium.

3. The system of any of the proceeding embodiments, wherein the roughed surface is diamond-bit coated.

4. The system of any of the proceeding embodiments, wherein the circumference of the roughened outer surface has a diameter of 1 mm or less to allow for in-vivo insertion within a body of a patient.

5. The system of any of the proceeding embodiments: wherein the rotational actuator is configured to drive rotation of the probe at a fixed torque; and wherein the sensor is configured to measure rotational displacement of the probe as a result of resistance generated from the viscoelastic medium.

6. The system of any of the proceeding embodiments: wherein the rotational actuator is configured to drive rotation of the probe at a fixed speed; and wherein the sensor is configured to measure torque applied the probe as a result of resistance generated from the viscoelastic medium.

7. The system of any of the proceeding embodiments, further comprising: a processor coupled to the sensor; programming executable on the processor for: (a) receiving data acquired by the sensor, said data relating to said measurements; and (b) generating a fluidic model of the viscoelastic medium, wherein the fluidic model is configured to characterize one or more viscoelastic properties of the viscoelastic medium.

8. The system of any of the proceeding embodiments, wherein the fluidic model is configured to calculate one or more of the elasticity and viscosity of the viscoelastic medium.

9. The system of any of the proceeding embodiments, wherein the programming is configured to measure creep compliance from rotational displacement measurements of the sensor.

10. The system of any of the proceeding embodiments, wherein the programming is configured to determine a rheological property of the viscoelastic medium selected from the group of properties consisting of: Relaxation Modulus, Creep Compliance, Complex Modulus, Storage Modulus, Loss Modulus, Complex Compliance, Storage Compliance, Loss Compliance, Equilibrium Modulus, Glass-like modulus, Equilibrium Compliance, Glasslike Compliance, Steady State Compliance, Steady-Flow Viscosity, and Dynamic Viscosity.

11. The system of any of the proceeding embodiments: wherein the circumference of the roughened outer surface has a diameter of 1 mm or less to allow for in-vivo insertion within a body fluid of a patient; and wherein the programming is further configured for comparing the fluidic model against a database of body fluid data to diagnose the risk or the presence of a degenerative or pathologic modification of the body fluid related to known or unknown diseases.

12. The system of any of the proceeding embodiments: wherein the probe is configured for minimally invasive in-vivo placement within the vitreous humor of the eye; and wherein the programming is further configured for comparing the fluidic model against a database of vitreous fluid data to determine a vitreous related pathology.

13. The system of any of the proceeding embodiments, wherein the pathology is selected from the group of pathologies consisting of retinal tear, rhegmatogenous or tractional retinal detachment, retinal edema, choroidal detachment, vitreous hemorrhage, and glaucoma.

14. The system of any of the proceeding embodiments; wherein the probe is configured for minimally invasive in-vivo placement within the vitreous humor of the eye; and wherein the programming is further configured for comparing the fluidic model against a database of vitreous fluid data to quantify the effects of an agent or device used for treating the vitreous humor.

15. A method for obtaining rheological properties of viscoelastic medium, the method comprising: inserting a distal end of a needle-like probe into the viscoelastic medium; the distal end of the probe having a roughened outer circumferential surface extending axially along at least a portion of the distal end; rotating the probe within the viscoelastic medium; wherein the roughed surface is configured to minimize slippage of the probe with respect to the viscoelastic medium when the probe is rotating within the medium; and sensing an imparted resistance to rotation of the probe within the viscoelastic medium.

16. The method of any of the proceeding embodiments, further comprising: driving rotation of the probe at a fixed torque; and measuring rotational displacement of the probe as a result of resistance generated from the viscoelastic medium.

17. The method of any of the proceeding embodiments, further comprising: driving rotation of the probe at a fixed speed; and measuring a torque applied to the probe as a result of resistance generated from the viscoelastic medium.

18. The method of any of the proceeding embodiments, further comprising: generating a fluidic model of the viscoelastic medium, wherein the fluidic model is configured to characterize one or more viscoelastic properties of the viscoelastic medium.

19. The method of any of the proceeding embodiments, wherein the circumference of the roughened outer surface has a diameter of 1 mm or less, the method further comprising: inserting the probe in-vivo within a body fluid of a patient.

20. The method of any of the proceeding embodiments, further comprising: calculating one or more of the elasticity and viscosity of the viscoelastic medium from the fluidic model.

21. The method of any of the proceeding embodiments, further comprising: measuring creep compliance from rotational displacement measurements of the sensor.

22. The method of any of the proceeding embodiments, further comprising: determining a rheological property of the viscoelastic medium selected from the group of properties consisting of: Relaxation Modulus, Creep Compliance, Complex Modulus, Storage Modulus, Loss Modulus, Complex Compliance, Storage Compliance, Loss Compliance, Equilibrium Modulus, Glass-like modulus, Equilibrium Compliance, Glasslike Compliance, Steady State Compliance, Steady-Flow Viscosity, and Dynamic Viscosity.

23. The method of any of the proceeding embodiments, further comprising: comparing the fluidic model against a database of body fluid data to diagnose the risk or the presence of a degenerative or pathologic modification of the body fluid related to known or unknown diseases.

24. The method of any of the proceeding embodiments, further comprising: comparing the fluidic model against a database of vitreous fluid data to determine a vitreous related pathology.

25. The method of any of the proceeding embodiments, wherein the pathology is selected from the group of pathologies consisting of retinal tear, rhegmatogenous or tractional retinal detachment, retinal edema, choroidal detachment, vitreous hemorrhage, and glaucoma.

26. The method of any of the proceeding embodiments, further comprising: comparing the fluidic model against a database of vitreous fluid data to quantify the effects of an agent or device used for treating the vitreous humor.

27. A method for in-vivo characterization of human body fluid, the method comprising: inserting a distal end of a needle-like probe into a body fluid of a patient; the distal end of the probe having a roughened outer circumferential surface extending axially along at least a portion of the distal end; rotating the probe within the body fluid; wherein the roughed surface is configured to minimize slippage of the probe with respect to the body fluid when the probe is rotating within the body fluid; and sensing an imparted resistance to rotation of the probe within the body fluid.

28. The method of any of the proceeding embodiments, further comprising: generating a fluidic model of the viscoelastic medium, wherein the fluidic model is configured to characterize one or more viscoelastic properties of the viscoelastic medium.

29. The method of any of the proceeding embodiments, further comprising: comparing the fluidic model against a database of vitreous fluid data to determine a vitreous related pathology.

30. The method of any of the proceeding embodiments, wherein the pathology is selected from the group of pathologies consisting of retinal tear, rhegmatogenous or tractional retinal detachment, retinal edema, choroidal detachment, vitreous hemorrhage, and glaucoma.

31. The method of any of the proceeding embodiments, further comprising: comparing the fluidic model against a database of vitreous fluid data to quantify the effects of an agent or device used for treating the vitreous humor.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Liquid | $\eta_{rod}$ (Pa · s) | $\eta_{plate}$ (Pa · s) | $\eta_{flow}$ (Pa · s) |
|---|---|---|---|
| Silicone Oil 61 | 933.33 | 1011.10 | 982.07 |
| Polystyrene 0.25 | 90.11 | 93.26 | 91.78 |
| Oligomer | 8.65 | 8.84 | 8.53 |
| Silicone Oil 41 | 100.55 | 105.41 | 105.60 |

We claim:

1. A system for obtaining rheological properties of viscoelastic medium, the system comprising:
    a needle-like probe having a distal and a proximal end;
    a rotational actuator;
    a sensor coupled to the rotational actuator;
    the proximal end of the probe configured for attachment to the rotational actuator;
    the distal end of the probe having a roughened outer circumferential surface extending axially along at least a portion of the distal end;
    wherein the distal end of the probe is configured to be disposed within the viscoelastic medium;
    wherein the sensor is configured to obtain measurements corresponding to rotation of the probe within the viscoelastic medium;
    a processor coupled to the sensor;
    programming executable on the processor for:
        (a) receiving data acquired by the sensor, said data relating to said measurements;
        (b) generating a fluidic model of the viscoelastic medium;
        (c) wherein the fluidic model is configured to characterize one or more viscoelastic properties of the viscoelastic medium; and
        (d) measuring creep compliance from rotational displacement measurements of the sensor.

2. A system as recited in claim 1, wherein the roughened outer circumferential surface is configured to minimize slippage of the probe with respect to the viscoelastic medium when the probe is rotating within the medium.

3. A system as recited in claim 2, wherein the roughened outer circumferential surface is diamond-bit coated.

4. A system as recited in claim 1, wherein the circumference of the roughened outer surface has a diameter of 1 mm or less to allow for in-vivo insertion within a body of a patient.

5. A system as recited in claim 1:
    wherein the rotational actuator is configured to drive rotation of the probe at a fixed torque; and
    wherein the sensor is configured to measure rotational displacement of the probe as a result of resistance generated from the viscoelastic medium.

6. A system as recited in claim 1:
    wherein the rotational actuator is configured to drive rotation of the probe at a fixed speed; and
    wherein the sensor is configured to measure torque applied the probe as a result of resistance generated from the viscoelastic medium.

7. A system as recited in claim 1, wherein the fluidic model is configured to calculate one or more of the elasticity and viscosity of the viscoelastic medium.

8. A system as recited in claim 1, wherein the programming is configured to determine a rheological property of the viscoelastic medium selected from the group of properties consisting of: Relaxation Modulus, Creep Compliance, Complex Modulus, Storage Modulus, Loss Modulus, Complex Compliance, Storage Compliance, Loss Compliance, Equilibrium Modulus, Glass-like modulus, Equilibrium Compliance, Glasslike Compliance, and Steady State Compliance.

9. A system as recited in claim 1:
wherein the circumference of the roughened outer surface has a diameter to allow for in-vivo insertion within a body fluid of a patient; and
wherein the programming is further configured for comparing the fluidic model against a database of body fluid data to diagnose the risk or the presence of a degenerative or pathologic modification of the body fluid related to known or unknown diseases.

10. A system as recited in claim 9:
wherein the probe is configured for minimally invasive in-vivo placement within the vitreous humor of the eye; and
wherein the programming is further configured for comparing the fluidic model against a database of vitreous fluid data to determine a vitreous related pathology.

11. A system as recited in claim 10, wherein the pathology is selected from the group of pathologies consisting of retinal tear, rhegmatogenous or tractional retinal detachment, retinal edema, choroidal detachment, vitreous hemorrhage, and glaucoma.

12. A system as recited in claim 9;
wherein the probe is configured for minimally invasive in-vivo placement within the vitreous humor of the eye; and
wherein the programming is further configured for comparing the fluidic model against a database of vitreous fluid data to quantify the effects of an agent or device used for treating the vitreous humor.

13. A system for obtaining rheological properties of viscoelastic medium, the system comprising:
a needle-like probe having a distal and a proximal end;
a rotational actuator;
a sensor coupled to the rotational actuator;
the proximal end of the probe configured for attachment to the rotational actuator;
the distal end of the probe having a roughened outer circumferential surface extending axially along at least a portion of the distal end;
wherein the roughened outer circumferential surface has a diameter to allow for in-vivo insertion within a body fluid of a patient comprising the viscoelastic medium;
wherein the distal end of the probe is configured to be disposed within the viscoelastic medium;
wherein the sensor is configured to obtain measurements corresponding to rotation of the probe within the viscoelastic medium;
a processor coupled to the sensor;
programming executable on the processor for:
(a) receiving data acquired by the sensor, said data relating to said measurements;
(b) generating a fluidic model of the viscoelastic medium; and
(c) comparing the fluidic model against a database of body fluid data to diagnose the risk or the presence of a degenerative or pathologic modification of the body fluid related to known or unknown diseases.

14. A system as recited in claim 13, wherein the roughened outer circumferential surface is configured to minimize slippage of the probe with respect to the viscoelastic medium when the probe is rotating within the medium.

15. A system as recited in claim 14, wherein the roughened outer circumferential surface is diamond-bit coated.

16. A system as recited in claim 13, wherein the circumference of the roughened outer surface has a diameter of 1 mm or less to allow for in-vivo insertion within a body of a patient.

17. A system as recited in claim 13:
wherein the rotational actuator is configured to drive rotation of the probe at a fixed torque; and
wherein the sensor is configured to measure rotational displacement of the probe as a result of resistance generated from the viscoelastic medium.

18. A system as recited in claim 13:
wherein the rotational actuator is configured to drive rotation of the probe at a fixed speed; and
wherein the sensor is configured to measure torque applied the probe as a result of resistance generated from the viscoelastic medium.

19. A system as recited in claim 13, wherein the fluidic model is configured to calculate one or more of the elasticity and viscosity of the viscoelastic medium.

20. A system as recited in claim 13, wherein the programming is configured to measure creep compliance from rotational displacement measurements of the sensor.

21. A system as recited in claim 13, wherein the programming is configured to determine a rheological property of the viscoelastic medium selected from the group of properties consisting of: Relaxation Modulus, Creep Compliance, Complex Modulus, Storage Modulus, Loss Modulus, Complex Compliance, Storage Compliance, Loss Compliance, Equilibrium Modulus, Glass-like modulus, Equilibrium Compliance, Glasslike Compliance, and Steady State Compliance.

22. A system as recited in claim 13:
wherein the probe is configured for minimally invasive in-vivo placement within the vitreous humor of the eye; and
wherein the programming is further configured for comparing the fluidic model against a database of vitreous fluid data to determine a vitreous related pathology.

23. A system as recited in claim 22, wherein the pathology is selected from the group of pathologies consisting of retinal tear, rhegmatogenous or tractional retinal detachment, retinal edema, choroidal detachment, vitreous hemorrhage, and glaucoma.

24. A system as recited in claim 13:
wherein the probe is configured for minimally invasive in-vivo placement within the vitreous humor of the eye; and
wherein the programming is further configured for comparing the fluidic model against a database of vitreous fluid data to quantify the effects of an agent or device used for treating the vitreous humor.

* * * * *